(12) United States Patent
Mujwid et al.

(10) Patent No.: US 12,740,864 B2
(45) Date of Patent: Sep. 22, 2026

(54) INFLATABLE PENILE PROSTHESIS WITH GUIDES IN VALVE OF PUMP ASSEMBLY

(71) Applicant: Boston Scientific Scimed, Inc., Maple Grove, MN (US)

(72) Inventors: James Ryan Mujwid, Hudson, WI (US); John Anders Bostrom, Minneapolis, MN (US); Mark Edward DiLoreto, Chaska, MN (US); Ryan Earl Fredrick, Eden Prairie, MN (US); Travis J. Schauer, Rockford, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 944 days.

(21) Appl. No.: 18/064,646

(22) Filed: Dec. 12, 2022

(65) Prior Publication Data

US 2023/0109586 A1 Apr. 6, 2023

Related U.S. Application Data

(63) Continuation of application No. 16/947,473, filed on Aug. 3, 2020, now Pat. No. 11,547,566.

(Continued)

(51) Int. Cl.
*A61F 2/26* (2006.01)

(52) U.S. Cl.
CPC ........ *A61F 2/26* (2013.01); *A61F 2230/0067* (2013.01); *A61F 2230/0069* (2013.01)

(58) Field of Classification Search
None
See application file for complete search history.

(56) References Cited

U.S. PATENT DOCUMENTS 4,222,377 A * 9/1980 Burton .................... A61F 2/004 600/38
4,566,446 A * 1/1986 Fogarty ..................... A61F 2/26 600/40

(Continued)

FOREIGN PATENT DOCUMENTS

CN 101351173 A 1/2009
WO 2019199722 A1 10/2019

OTHER PUBLICATIONS

First Office Action for Chinese Application No. 202080056161.6 (with English translation), mailed Dec. 31, 2024, 19 pages.

(Continued)

*Primary Examiner* — Christine H Matthews
(74) *Attorney, Agent, or Firm* — Brake Hughes Bellermann LLP

(57) ABSTRACT

An inflatable penile prosthesis can comprise a reservoir, an inflatable member, and a pump assembly. The pump assembly can include at least one valve comprising an entry tube interface configured to attach to the entry tube and defining an entry passageway, an entry portion adjacent to the entry tube interface, a middle portion adjacent to the entry portion, an exit portion adjacent to the middle portion, the exit portion being narrower than the middle portion, the exit portion defining an exit portion passageway and comprising multiple guides extending toward a longitudinal exit axis, the multiple guides being symmetrical about the longitudinal exit axis, the exit tube interface adjacent to the exit portion, and a poppet disposed inside the chamber, the poppet being biased to rest against the entry portion.

20 Claims, 18 Drawing Sheets

Related U.S. Application Data

(60) Provisional application No. 62/883,207, filed on Aug. 6, 2019.

(56) References Cited

U.S. PATENT DOCUMENTS

| | | | |
|---|---|---|---|
| 4,699,128 | A | 10/1987 | Hemmeter et al. |
| 4,895,139 | A | 1/1990 | Hauschild et al. |
| 5,010,882 | A | 4/1991 | Polyak et al. |
| 5,141,509 | A | 8/1992 | Burton et al. |
| 6,240,962 | B1 | 6/2001 | Tai et al. |
| 6,334,761 | B1 | 1/2002 | Tai et al. |
| 8,062,209 | B2 | 11/2011 | Rowland et al. |
| 8,109,870 | B2 | 2/2012 | Kuyava et al. |
| 8,568,294 | B2 | 10/2013 | Ellering |
| 8,617,052 | B2 | 12/2013 | Fogarty |
| 8,632,456 | B2 | 1/2014 | Fogarty et al. |
| 8,932,203 | B2 | 1/2015 | Ellering |
| 8,932,204 | B2 | 1/2015 | Fogarty et al. |
| 8,939,889 | B1 | 1/2015 | Chechik |
| 8,974,370 | B2 | 3/2015 | Chechik |
| 9,186,251 | B2 | 11/2015 | Fogarty et al. |
| 11,285,006 | B2 | 3/2022 | Mujwid et al. |
| 2002/0082471 | A1 | 6/2002 | Henkel et al. |
| 2002/0082473 | A1 | 6/2002 | Henkel et al. |
| 2007/0142700 | A1 | 6/2007 | Fogarty et al. |
| 2008/0114202 | A1 | 5/2008 | Kuyava et al. |
| 2010/0056859 | A1 | 3/2010 | Kuyava et al. |
| 2013/0072751 | A1 | 3/2013 | Fogarty |
| 2013/0303841 | A1 | 11/2013 | Fogarty |
| 2018/0071101 | A1 | 3/2018 | Daniel |
| 2019/0307567 | A1 | 10/2019 | Mujwid et al. |

OTHER PUBLICATIONS

International Search Report and Written Opinion for PCT Application No. PCT/US2020/070356, mailed on Nov. 18, 2020, 12 pages.

* cited by examiner

INFLATABLE PENILE PROSTHESIS WITH GUIDES IN VALVE OF PUMP ASSEMBLY

CROSS-REFERENCE TO RELATED APPLICATIONS

This application is a continuation of, and claims priority to, U.S. patent application Ser. No. 16/947,473, filed on Aug. 3, 2020, entitled "INFLATABLE PENILE PROSTHESIS WITH GUIDES IN VALVE OF PUMP ASSEMBLY", which claims priority to U.S. Patent Application No. 62/883,207, filed on Aug. 6, 2019, entitled "INFLATABLE PENILE PROSTHESIS WITH GUIDES IN VALVE OF PUMP ASSEMBLY", the disclosures of which are incorporated by reference herein in their entirety.

TECHNICAL FIELD

This description relates to bodily implants and more specifically to bodily implants, such as a penile prosthesis that includes a refill valve and/or an inflation valve.

BACKGROUND

One treatment for male erectile dysfunction is the implantation of a penile prosthesis that mechanically erects the penis. Some existing penile prostheses include inflatable cylinders or members that can be inflated or deflated using a pump mechanism. The pump mechanism pulls fluid from a fluid reservoir and then transfers the fluid to the inflatable members. In some existing devices, the pump mechanism includes a pump bulb that creates a vacuum by expanding after a manual compression, which is applied by a patient or physician. This expansion creates negative pressure (vacuum) pulling fluid through a refill valve (from the fluid reservoir to the pump bulb). Then, compression of the pump bulb results in pressure rising in the pump bulb until the point at which an inflation valve opens which allows the fluid to transfer out of the pump valve and into the inflatable cylinders. In some existing devices, which focused on maximizing efficiencies through fluid pathways, oscillation results in noise and vibration within the pump. The noise can be annoying, unnatural, and/or non-discrete to the patient.

SUMMARY

An inflatable penile prosthesis can comprise a reservoir configured to hold fluid, an inflatable member, and a pump assembly. The pump assembly can be configured to transfer fluid from the reservoir to the inflatable member, the pump assembly comprising a pump bulb, at least one valve, an entry tube configured to provide the fluid to the at least one valve, and an exit tube configured to send the fluid from the at least one valve, the pump bulb being configured to transfer the fluid from the reservoir, through the at least one valve, and to the inflatable member in response to the pump bulb being compressed. The at least one valve can comprise an entry tube interface configured to attach to the entry tube and defining an entry passageway, an entry portion adjacent to the entry tube interface, the entry portion being circular about a longitudinal entry portion axis and defining an entry portion passageway, the longitudinal entry portion axis being parallel to a direction from which the entry tube interface extends from the entry portion, a middle portion adjacent to the entry portion, the middle portion being wider than the entry portion and defining a chamber, an exit portion adjacent to the middle portion, the exit portion being narrower than the middle portion, the exit portion defining an exit portion passageway and comprising multiple guides extending toward a longitudinal exit axis, the longitudinal exit axis extending through a center of the exit portion parallel to a direction that an exit tube interface extends from the exit portion, the multiple guides being symmetrical about the longitudinal exit axis, the exit tube interface adjacent to the exit portion, the exit tube interface being configured to attach to the exit tube, the exit tube interface being narrower than the middle portion, the exit tube interface defining an exit passageway, and a poppet disposed inside the chamber, the poppet being biased to rest against the entry portion.

An inflatable penile prosthesis can comprise a reservoir configured to hold fluid, an inflatable member, and a pump assembly. The pump assembly can be configured to transfer fluid from the reservoir to the inflatable member, the pump assembly comprising a pump bulb, at least one valve, an entry tube configured to provide the fluid to the at least one valve, and an exit tube configured to send the fluid from the at least one valve, the pump bulb being configured to transfer the fluid from the reservoir, through the at least one valve, and to the inflatable member in response to the pump bulb being compressed. The at least one valve can comprise an entry tube interface configured to attach to the entry tube and defining an entry passageway, an entry portion adjacent to the entry tube interface, the entry portion being circular about a longitudinal entry portion axis and defining an entry portion passageway, the longitudinal entry portion axis being parallel to a direction from which the entry tube interface extends from the entry portion, a middle portion adjacent to the entry portion, the middle portion being wider than the entry portion and defining a chamber, an exit portion adjacent to the middle portion, the exit portion being narrower than the middle portion, the exit portion defining an exit portion passageway and comprising multiple guides extending toward a longitudinal exit axis, the longitudinal exit axis extending through a center of the exit portion parallel to a direction that an exit tube interface extends from the exit portion, the multiple guides being symmetrical about the longitudinal exit axis, the exit tube interface adjacent to the exit portion, the exit tube interface being configured to attach to the exit tube, the exit tube interface being narrower than the middle portion, the exit tube interface defining an exit passageway, a poppet disposed inside the chamber, and a biasing member biasing the poppet to rest against the entry portion.

An inflatable penile prosthesis can comprise a reservoir configured to hold fluid, an inflatable member, and a pump assembly. The pump assembly can be configured to transfer fluid from the reservoir to the inflatable member, the pump assembly comprising a pump bulb, at least one valve, an entry tube configured to provide the fluid to the at least one valve, and an exit tube configured to send the fluid from the at least one valve, the pump bulb being configured to transfer the fluid from the reservoir, through the at least one valve, and to the inflatable member in response to the pump bulb being compressed. The at least one valve can comprise an entry tube interface configured to attach to the entry tube and defining an entry passageway, an entry portion adjacent to the entry tube interface, the entry portion being circular about a longitudinal entry portion axis and defining an entry portion passageway, the longitudinal entry portion axis being parallel to a direction from which the entry tube interface extends from the entry portion, a middle portion adjacent to the entry portion, the middle portion being wider than the entry portion and defining a chamber, an exit portion adjacent to the middle portion, the exit portion being narrower than the middle portion, the exit portion defining an exit portion passageway and comprising multiple guides extending toward a longitudinal exit axis, the longitudinal exit axis extending through a center of the exit portion parallel to a direction that an exit tube interface extends from the exit portion, the multiple guides being symmetrical about the longitudinal exit axis, the exit tube interface adjacent to the exit portion, the exit tube interface being configured to attach to the exit tube, the exit tube interface being narrower than the middle portion, the exit tube interface defining an exit passageway, and a poppet disposed inside the chamber, the poppet being biased to rest against the entry portion. The poppet can comprise a cap member, the cap member comprising a rounded portion facing toward the entry portion, an exit stem extending from a portion of the cap member opposite from the rounded portion, through the exit portion passageway, and into the exit passageway, the exit stem being cylindrically shaped, and an entry portion stem extending from the rounded portion, through the entry portion, and into the entry passageway. The cap member can define multiple grooves at equal intervals from each other, the multiple grooves extending in directions offset between thirty degrees (30°) and sixty degrees (60°) from a direction that the exit stem extends from the cap member.

The details of one or more implementations are set forth in the accompanying drawings and the description below. Other features will be apparent from the description and drawings, and from the claims.

DETAILED DESCRIPTION

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the present disclosure.

The terms "a" or "an," as used herein, are defined as one or more than one. The terms "including" and/or "having", as used herein, are defined as comprising (i.e., open transition). The term "coupled" or "moveably coupled," as used herein, is defined as connected, although not necessarily directly and mechanically.

In general, the embodiments are directed to medical devices such as penile prostheses or other bodily implants. The term patient may hereafter be used for a person who benefits from the medical device or the methods disclosed in the present disclosure. For example, the patient can be a person whose body is implanted with the medical device or the method disclosed for operating the medical device by the present disclosure. For example, in some embodiments, the patient may be a human male, a human female, or any other mammal.

The embodiments discussed herein provide a valve within an inflatable penile prosthesis that can reduce noise due to oscillation of a poppet within the valve.

Figure 1A:
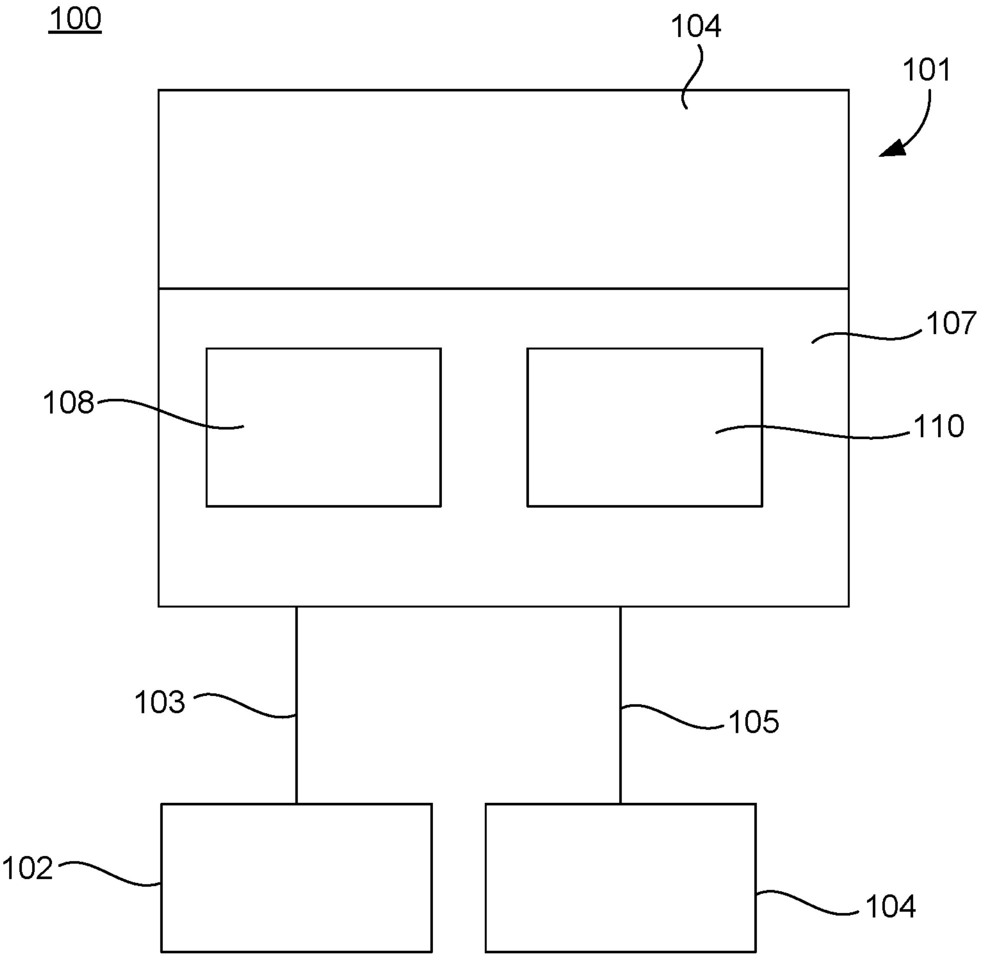
FIG. 1A schematically illustrates a penile prosthesis according to an aspect.

FIG. 1A schematically illustrates a penile prosthesis according to an aspect. The inflatable penile prosthesis 100 may include a reservoir 102, an inflatable member 104, and a pump assembly 101 configured to transfer fluid between the reservoir 102 and the inflatable member 104. In some examples, the inflatable member 104 may be implanted into the corpus cavernosae of the patent, the reservoir 102 may be implanted in the abdomen or pelvic cavity of the patient (e.g., the reservoir 102 may be implanted in the lower portion of the patient's abdominal cavity or the upper portion of the patient's pelvic cavity), and the pump assembly 101 may be implanted in the scrotum of the patient.

The inflatable member 104 may be capable of expanding upon the injection of fluid into a cavity of the inflatable member 104. For instance, upon injection of the fluid into the inflatable member 104, the inflatable member 104 may increase its length and/or width, as well as increase its rigidity. In some examples, the inflatable member 104 may include a pair of cylinders or at least two cylinders, e.g., a first cylinder member and a second cylinder member. The volumetric capacity of the inflatable member 104 may depend on the size of the cylinders. In some examples, the volume of fluid in each cylinder may vary from about 10 milliliters in smaller cylinders and to about 50 milliliters in larger sizes. In some examples, the first cylinder member may be larger than the second cylinder member. In other examples, the first cylinder member may have the same size as the second cylinder member.

The reservoir 102 may include a container having an internal chamber configured to hold or house fluid that is used to inflate the inflatable member 104. The volumetric capacity of the reservoir 102 may vary depending on the size of the inflatable penile prosthesis 100. In some examples, the volumetric capacity of the reservoir 102 may be 3 to 150 cubic centimeters. In some examples, the reservoir 102 is constructed from the same material as the inflatable member 104. In other examples, the reservoir 102 is constructed from a different material than the inflatable member 104.

The inflatable penile prosthesis 100 may include a first conduit connector 103 and a second conduit connector 105. The conduit connectors 103, 105 can also be considered an entry tube for carrying fluid into a valve (described below) and an exit tube for carrying fluid from a valve. Each of the first conduit connector 103 and the second conduit connector 105 can define a lumen configured to transfer the fluid to and from the pump assembly 101. The first conduit connector 103 may be coupled to the pump assembly 101 and the reservoir 102 such that fluid can be transferred between the pump assembly 101 and the reservoir 102 via the first conduit connector 103. For example, the first conduit connector 103 may define a first lumen configured to transfer fluid between the pump assembly 101 and the reservoir 102. The first conduit connector 103 may include a single or multiple tube members for transferring the fluid between the pump assembly 101 and the reservoir 102.

The second conduit connector 105 can be coupled to the pump assembly 101 and the inflatable member 104 such that fluid can be transferred between the pump assembly 101 and the inflatable member 104 via the second conduit connector 105. For example, the second conduit connector 105 may define a second lumen configured to transfer fluid between the pump assembly 101 and the inflatable member 104. The second conduit connector 105 can include a single or multiple tube members for transferring the fluid between the pump assembly 101 and the inflatable member 104. In some examples, the first conduit connector 103 and the second conduit connector 105 can include a silicone rubber material.

The pump assembly 101 may switch between an inflation mode in which the fluid in the reservoir 102 is transferred to the inflatable member 104 through the pump assembly 101 in a first direction (e.g., inflation direction) and a deflation mode in which the fluid in the inflatable member 104 is transferred back to the reservoir 102 through the pump assembly 101 in a second direction (e.g., deflation direction).

The pump assembly 101 can include a pump bulb 106 and at least one valve, such as a valve body 107. In some examples, the pump bulb 106 may include a flexible member defining a cavity. In some examples, the pump bulb 106 may define a pump shell having a flexible bulb and a valve body connector, where the valve body connector is designed to fit at least partially over the valve body 107. In some examples, the pump bulb 106 may include a squeeze pump. In some examples, the pump bulb 106 may include a portion that is round or substantially round. In some examples, the pump bulb 106 may include ribbing or dimples to aid the patient in gripping the pump bulb 106. The pump bulb 106 may use suction and pressure to move the fluid in and out of the cavity of the pump bulb 106 in the inflation mode. For example, the patient may depress or squeeze the pump bulb 106 to expel the fluid out of the cavity, and, when the flexible member returns to its original shape, the resulting suction pushes the fluid into the cavity of the pump bulb 106. In some examples, the pump bulb 106 may have a bulb spring rate that is designed to refill the pump bulb 106 in a selected time frame.

The pump bulb 106 may be squeezed or depressed by the patient in order to facilitate the transfer of fluid from the reservoir 102 to the inflatable member 104. For example, in the inflation mode, while the patient is operating the pump bulb 106, the pump bulb 106 may receive the fluid from the reservoir 102, and then output the fluid to the inflatable member 104. When the patient switches the pump bulb 106 to the deflation mode, at least some of the fluid can automatically be transferred back to the reservoir 102 (due to the difference in pressure from the inflatable member 104 to the reservoir 102). Then, the patient may squeeze the inflatable member 104 to facilitate the further transfer of fluid through the pump bulb 106 to the reservoir 102.

The valve body 107 can include at least one valve, such as a refill valve 108 and/or an inflation valve 110. The valve body 107 may define a first fluid passageway that connects the pump bulb 106 to the first conduit connector 103. The first fluid passageway may be a cavity that extends through the valve body 107. The first fluid passageway may define a cylindrical cavity having sections with different diameters. The refill valve 108 is disposed within at least one of the sections of the first fluid passageway. The valve body 107 may define a second fluid passageway that connects the pump bulb 106 to the second conduit connector 105. The second fluid passageway may be a cavity that extends through the valve body 107. The second fluid passageway is separate from the first fluid passageway. The second fluid passageway may define a cylindrical cavity having sections with different diameters. The inflation valve 110 is disposed within at least one of the sections of the second fluid passageway.

The refill valve 108 moves within the first fluid passageway between an open position and a closed position (or sealing position). The refill valve 108 can include a biasing member to return a poppet to the sealing position. The biasing member can bias the refill valve to the closed and/or sealed position. Fluid flowing from the reservoir 102 to the pump bulb 106 can overcome the force of the biasing member and move the refill valve to an open position, allowing fluid to flow through the refill valve 108. Fluid flowing from the pump bulb 106 to the reservoir 102, or no fluid flowing through the refill valve 108, can cause the refill valve 108 to close and/or seal.

The inflation valve 110 moves within the second fluid passageway between an open position and a closed position (or sealing position), and a biasing member is used to bias the inflation valve 110 to the sealing position. In some examples, the biasing member is a spring. The inflation valve 110 may provide a reliable seal in order to maintain fluid pressure within the inflatable member 104, but also allow fluid in during inflation of the inflatable member 104. The pump bulb 106 can transfer the fluid from the reservoir 102, through the at least one valve 108, 110, and to the inflatable member 104 in response to the pump bulb 106 being compressed. When the patient compresses the pump bulb 106, the pressure increases within the pump bulb 106 and eventually opens the inflation valve 110, thereby allowing fluid to pass over the inflation valve 110. The initial opening of the inflation valve 110 requires compression of the pump bulb 106, resulting in a pressure spike that opens the inflation valve 110. Keeping the inflation valve 110 open is dependent on the pressure differential over the inflation valve seat, which is determined by the application of force by the patient in addition to spring preload/rate and downstream flow resistance.

Figure 1B:
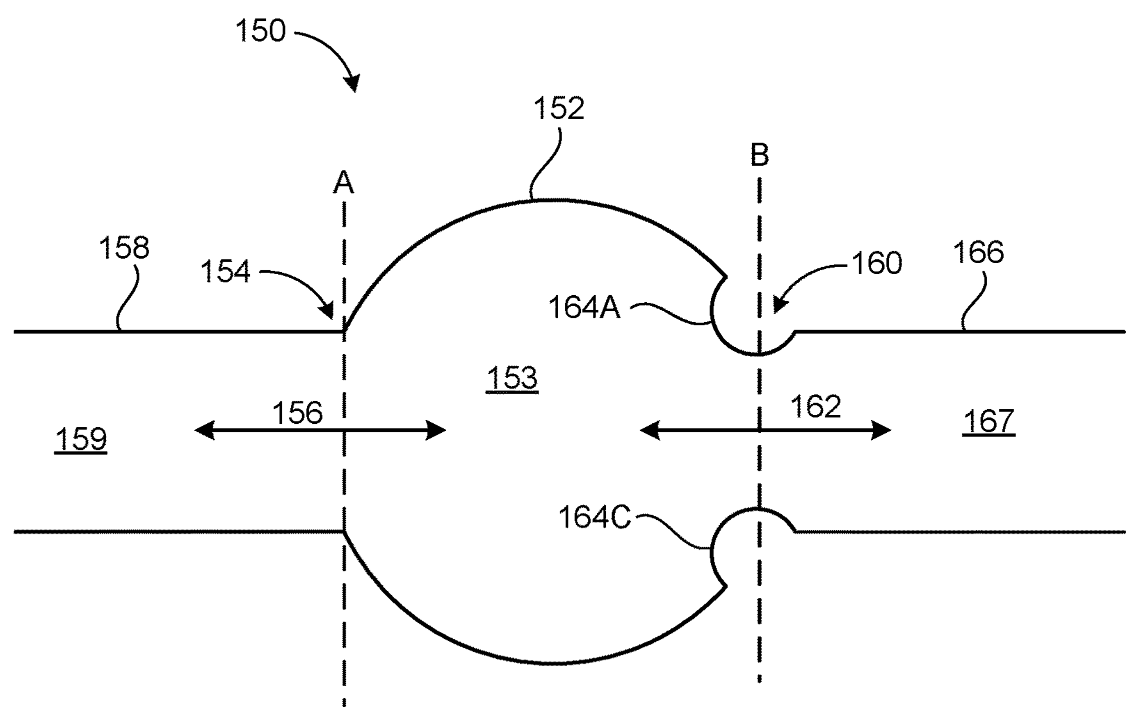
FIG. 1B illustrates a valve included in the penile prosthesis according to an aspect.

FIG. 1B illustrates a valve 150 included in the penile prosthesis 100 according to an aspect. The valve 150 can represent either the refill valve 108 or the inflation valve 110. FIG. 1B is a cross-sectional view of the valve 150.

The valve 150 can include an entry tube interface 158, a base 154 and/or entry portion adjacent to the entry tube interface 158, a bulb 152 and/or middle portion adjacent to the base 154, a tail 160 and/or exit portion adjacent to the bulb 152, and an exit tube interface 166 adjacent to the tail 160.

The entry tube interface 158 can be configured to attach to, and/or can be attached to, an entry tube. The entry tube can carry fluid into the valve 150 and can include either of the first or second conduit connectors 103, 105. The entry tube interface 158 can be narrower than the bulb 152. The entry tube interface 158 can define an entry passageway 159 via which fluid can flow into the valve 150 and/or bulb 152 from the entry tube.

The base 154 can be circular about a longitudinal base axis 156 and/or longitudinal entry portion axis. The longitudinal base axis 156 can extend parallel to a direction in which the entry tube interface 158 extends from the base 154. The base 154 can define a base passageway 155 (labeled in FIG. 1D) and/or entry portion passageway. Fluid can flow between the entry passageway 159 and the bulb 152 via the base passageway 155. A poppet 168 (shown in FIG. 1C) can rest against the base 154, closing and/or sealing the valve 150.

The bulb 152 can be wider than both the entry tube interface 158 and the exit tube interface 166. The bulb 152 can define a chamber 153. The poppet 168 can reside in the chamber 153. Fluid can flow through the chamber 153 from the entry tube interface 158 into the exit tube interface 166.

The tail 160 can be narrower than the bulb 152. The tail 160 can define a tail passageway 161 (labeled in FIG. 1E) and/or exit portion passageway through which fluid can flow between the chamber 153 and an exit passageway 167 defined by the exit tube interface 166.

The tail 160 can include multiple guides 164A, 164C, of which two are shown in FIG. 1B. The guides 164A, 164C can extend into the chamber 153, into the tail passageway 161 (labeled in FIG. 1E), and/or toward a longitudinal tail axis 162. The longitudinal tail axis 162 can extend through a center of the tail 160 parallel to a direction that the exit tube interface 166 extends from the tail 160. The multiple guides 164A, 164C can be symmetrical about the longitudinal tail axis 162. The guides 164A, 164C can be separated by intervals of, for example, ninety degrees (90°) in an example of four guides 164A, 164C, or one hundred twenty degrees (120°) in an example of three guides 164A, 164C.

The exit tube interface 166 can be configured to attach to, and/or can be attached to, an exit tube. The exit tube can carry fluid from the valve 150 and can include either of the first or second conduit connectors 103, 105. The exit tube interface 166 can be narrower than the bulb 152. The exit tube interface 166 can define an exit passageway 167 via which fluid can flow from the valve 150 and/or bulb 152 to the exit tube. The entry passageway 159, base passageway 155, chamber 153, tail passageway 161, and exit passageway 167 can collectively for a first or second fluid passageway described above with respect to FIG. 1A.

Figure 1C:
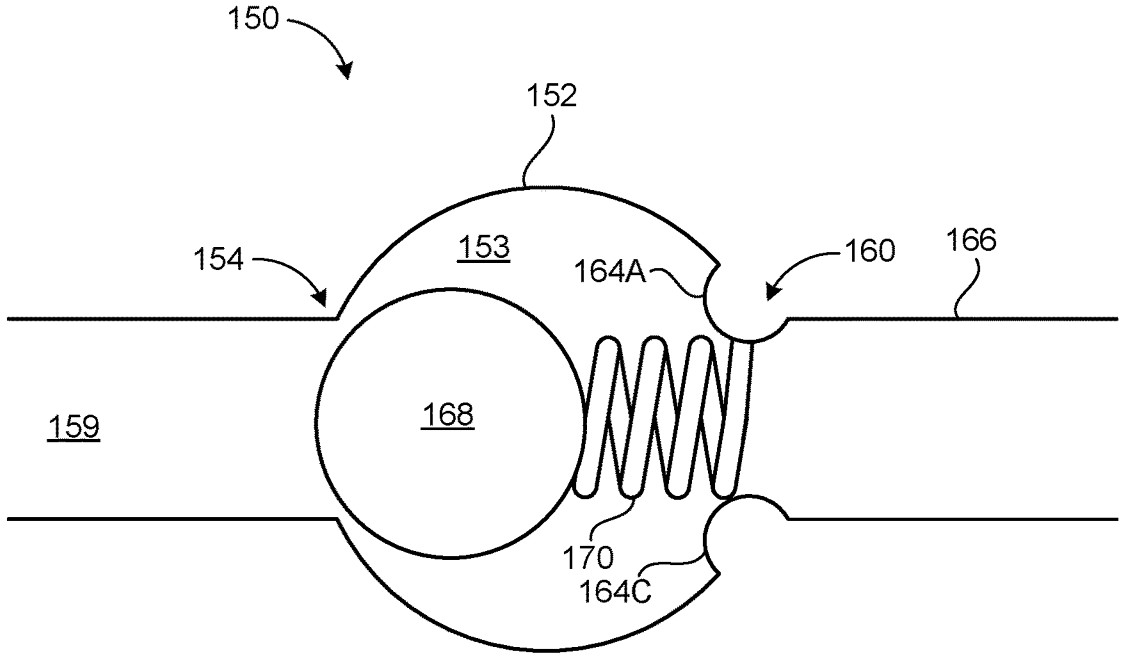
FIG. 1C illustrates the valve according to another aspect.

FIG. 1C illustrates the valve 150 according to another aspect. FIG. 1C is the same cross-sectional view of the valve 150 as FIG. 1B.

The poppet 168 can be included in the chamber 153. The poppet 168 can include at least one rounded portion that contacts and/or seals with the base 154, sealing and/or closing the valve 150. The poppet 168 can include various shapes, such as spherical, having a spherical member and a partial cone member extending from the spherical member, a cap member with a rounded portion facing toward the base 154 and a flat portion facing toward the tail 160 and a stem extending from the flat portion of the cap member, a spherical member with a cylindrical member extending from the spherical member and a partial cone member extending from the cylindrical member, or a cap member with a rounded portion and one or two stems extending from the cap member, as non-limiting examples. In some examples, the poppet 168 can include one or more grooves. Examples of the poppet 168 are shown in FIGS. 10A, 11A, 12A, 13A, 14A, and 15A.

The valve 150 can include a biasing member 170. The biasing member 170 can include a coil and/or spring. The biasing member 170 can be at least partially disposed within the chamber 153. The biasing member 170 can press and/or bias the poppet 168 toward and/or against the base 154, placing the valve 150 in the sealed and/or closed position, as described above with respect to FIG. 1A. The poppet 168 can press against the base 154 until fluid pressure from the entry passageway 159 presses the poppet 168 away from the base 154, opening the valve 150 and/or moving the valve 150 into the open position, as described above with respect to FIG. 1A. The biasing member 170 can be secured to the guides 164A, 164C, or other component of the valve 150.

Figure 1D:
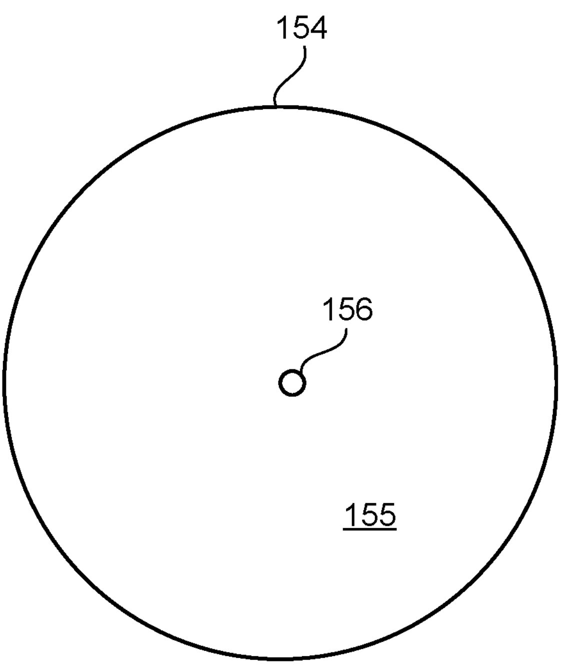
FIG. 1D illustrates the valve according to another aspect.

FIG. 1D illustrates the valve 150 according to another aspect. FIG. 1D is a cross-sectional view of the valve 150 along the line denoted 'A' in FIG. 1B. The base 154 can define the base passageway 155. The base axis 156 can extend through a center of the base 154.

Figure 1E:
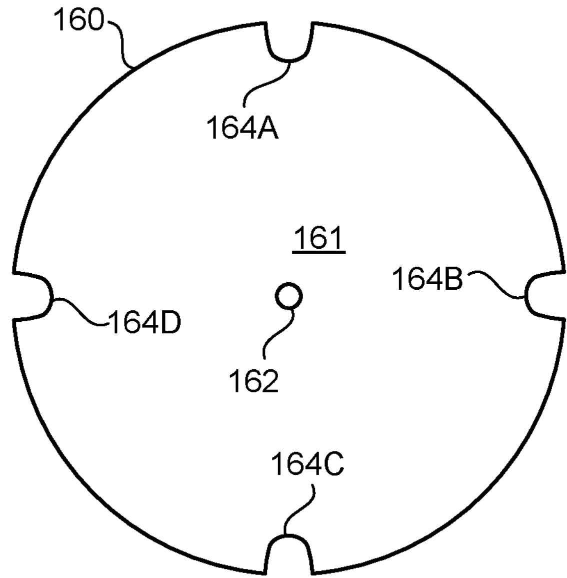
FIG. 1E illustrates the valve according to another aspect.

FIG. 1E illustrates the valve 150 according to another aspect. FIG. 1E is a cross-sectional view of the valve 150 along the line denoted 'B' in FIG. 1B. The tail 160 can define the tail passageway 161. The tail axis 162 can extend through the center of the tail 160. The guides 164A, 164B, 164C, 164D can extend toward the tail axis 162. The guides 164A, 164B, 164C, 164D can be symmetrical about the tail axis 162. The guides can be separated by intervals of 360° divided by the number of guides 164A, 164B, 164C, 164D. In the example shown in FIG. 1E in which the tail 160 includes four guides 164A, 164B, 164C, 164D, the guides 164A, 164B, 164C, 164D are separated by intervals of 90°. Fluid can flow through the spaces between the guides 164A, 164B, 164C, 164D even when fluid pressure presses the poppet 168 against the guides 164A, 164B, 164C, 164D. The guides 164A, 164B, 164C, 164D can reduce oscillation by the poppet 168, reducing noise and/or vibration emitted by the valve 150.

Figure 2:
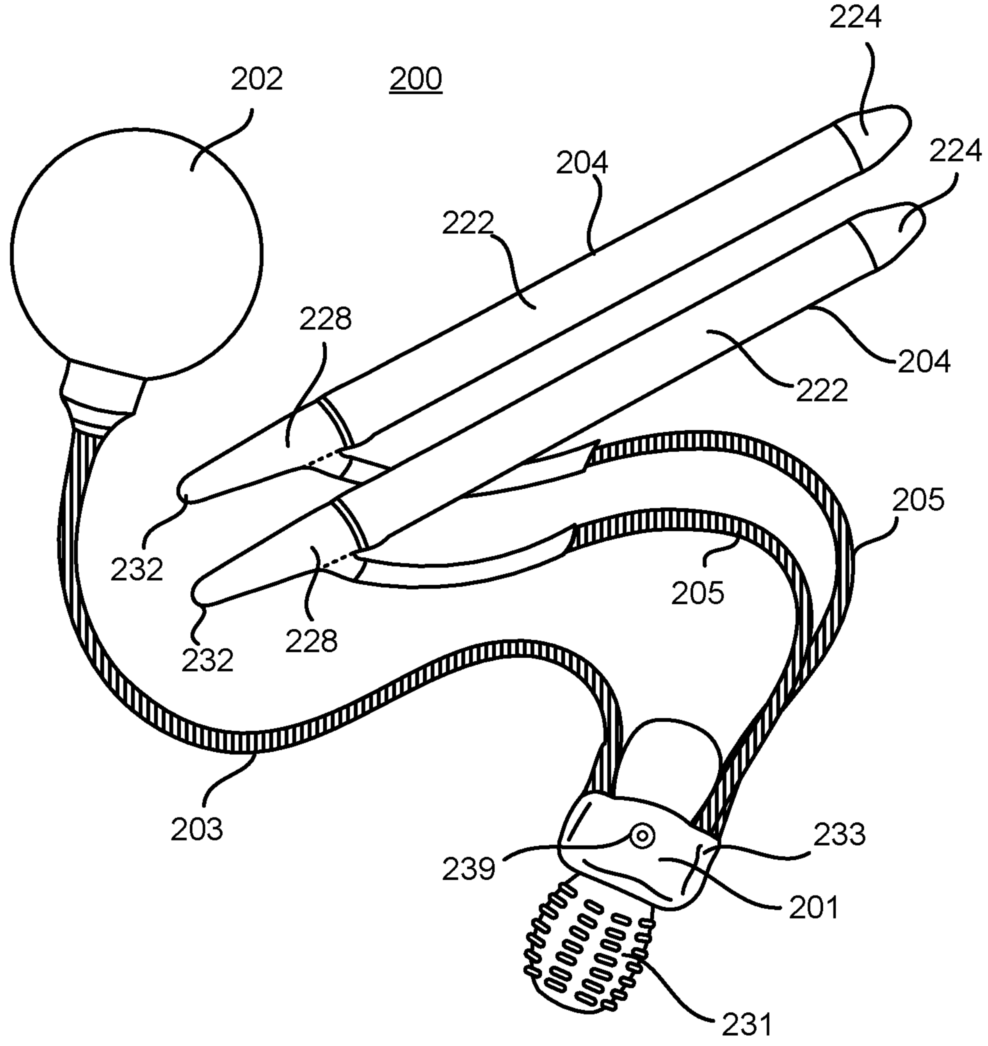
FIG. 2 illustrates a penile prosthesis according to another aspect.
Figure 3:
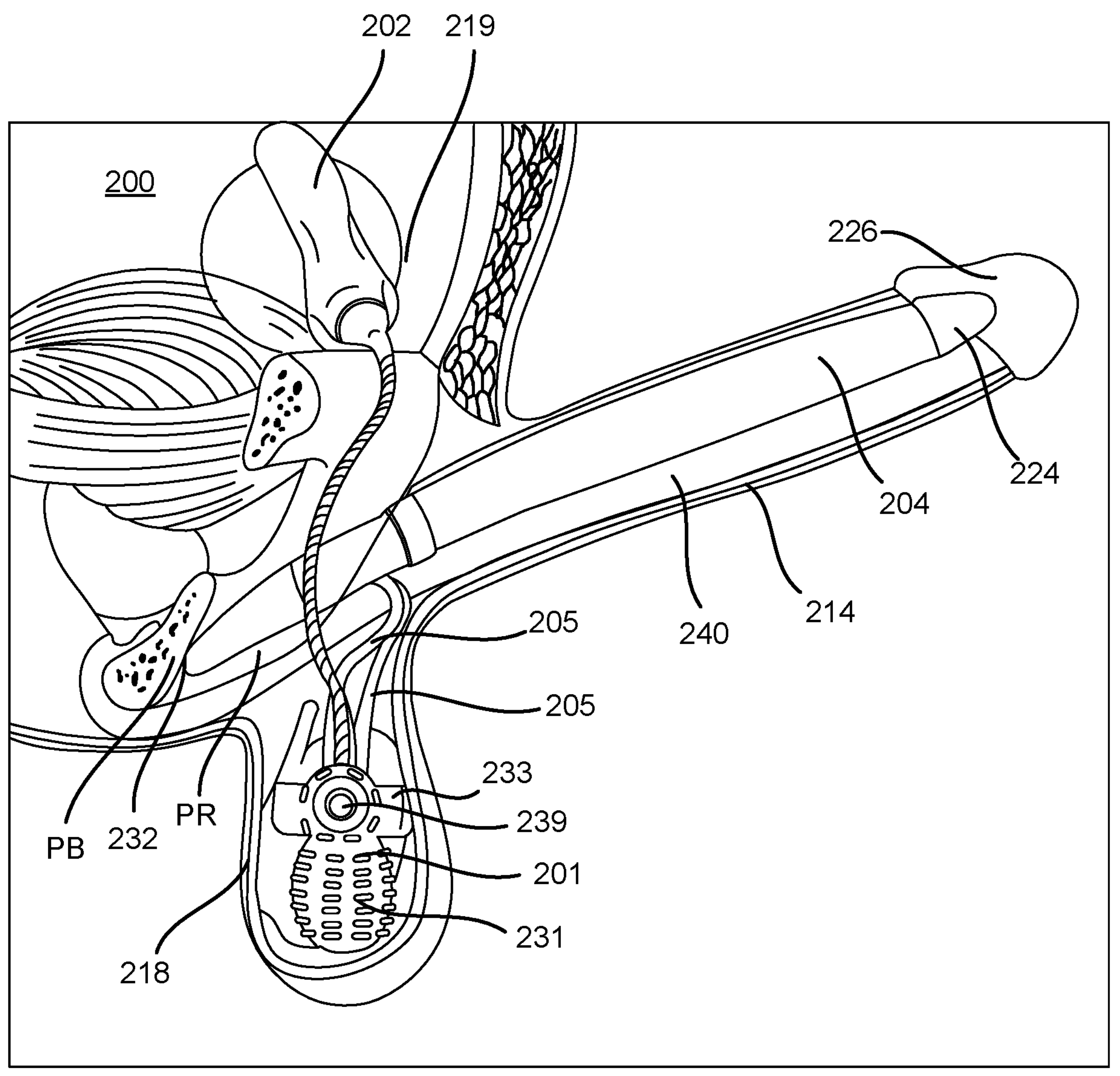
FIG. 3 illustrates a penile prosthesis placed within a body of a patient according to an aspect.

FIG. 2 illustrates a penile prosthesis 200 according to an aspect. FIG. 3 illustrates the penile prosthesis 200 placed within a body of a patient according to an aspect. The penile prosthesis 200 may include a pair of cylinders 204, and the pair of cylinders 204 or inflatable members are implanted in a penis 214. For example, one of the cylinders 204 may be disposed on one side of the penis 214. The other cylinder 204 (not shown in FIG. 3) of the pair of cylinders may be disposed on the other side of the penis 214. The cylinder 204 may include a first end portion 224, a cavity or inflation chamber 222, and a second end portion 228 having a rear tip 232.

The penile prosthesis 200 may include a pump assembly 201, which may be implanted into the patient's scrotum 218. A pair of conduit connectors 205 may attach the pump assembly 201 to the pair of inflatable members or cylinders 204 such that the pump assembly 201 is in fluid communication with the pair of inflatable members or cylinders 204. Also, the pump assembly 201 may be in fluid communication with a reservoir 202 via a conduit connector 203. The reservoir 202 may be implanted into the patient's abdomen 219. The inflation chamber 222 or portion of the cylinder 204 may be disposed within the penis 214. The first end portion 224 of the cylinder 204 may be at least partially disposed within the crown portion 226 of the penis 214. The second end portion 228 may be implanted into the patient's pubic region PR with the rear tip 232 proximate the pubic bone PB.

In order to implant the inflatable members or cylinders 204, the surgeon first prepares the patient. The surgeon often makes an incision in the penoscrotal region, e.g., where the base of the penis 214 meets with the top of the scrotum 218. From the penoscrotal incision, the surgeon may dilate the patient's corpus cavernosae 240 to prepare the patient to receive the pair of inflatable members or cylinders 204. The corpus cavernosum is one of two parallel columns of erectile tissue forming the dorsal part of the body of the penis 214, e.g., two slender columns that extend substantially the length of the penis 214. The surgeon will also dilate two regions of the pubic area to prepare the patient to receive the second end portion 228. The surgeon may measure the length of the corpora cavernosae from the incision and the dilated region of the pubic area to determine an appropriate size of the inflatable members or cylinders 204 to implant.

After the patient is prepared, the penile prosthesis 200 is implanted into the patient. The tip of the first end portion 224 of each cylinder 204 may be attached to a suture. The other end of the suture may be attached to a needle member (e.g., Keith needle). The needle member is inserted into the incision and into the dilated corpus cavernosum. The needle member is then forced through the crown of the penis 214. The surgeon tugs on the suture to pull the cylinder 204 into the corpus cavernosum. This is done for each cylinder of the pair of cylinders 204. Once the inflation chamber 222 is in place, the surgeon may remove the suture from the tip. The surgeon then inserts the second end portion 228. The surgeon inserts the rear end of the cylinder 204 into the incision and forces the second end portion 228 toward the pubic bone PB until each cylinder 204 is in place.

The pump assembly 201 includes a pump bulb 231, a valve body 233, and a selection member 239. The selection member 239 may be used to select or change the mode of the pump assembly 201. For example, the selection member 239 may be moved from a first position to a second position to place the device in its deflation mode. The selection member 239 may then be moved back from the second position to the first position to place the device in the inflation mode. In some embodiments, the selection member 239 is movable with respect to the valve body 233.

The pump bulb 231 may be squeezed or depressed by the patient in order to facilitate the transfer of fluid from the reservoir 202 to the cylinders 204. For example, in the inflation mode, while the patient is operating the pump bulb 231, the pump bulb 231 may receive the fluid from the reservoir 202, and then output the fluid to the cylinders 204. When the patient switches to the deflation mode, at least some of the fluid can automatically be transferred back to the reservoir 202 (due to the difference in pressure from the cylinders 204 to the reservoir 202). Then, the patient may squeeze the cylinders 204 to facilitate the further transfer of fluid through the pump bulb 231 to the reservoir 202.

Figure 4A:
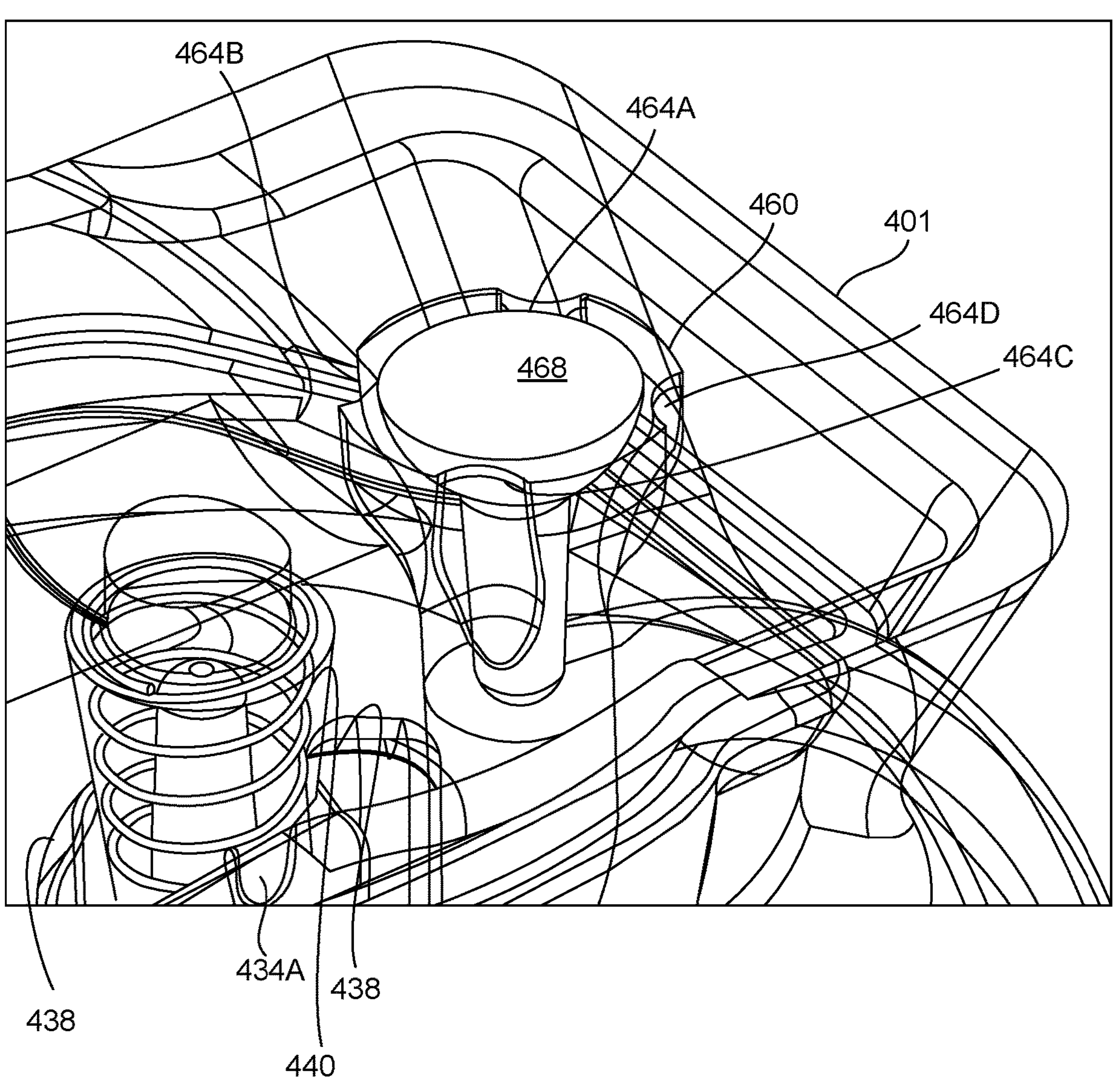
FIGS. 4A and 4B illustrate a portion of a pump assembly according to an aspect.
Figure 4B:
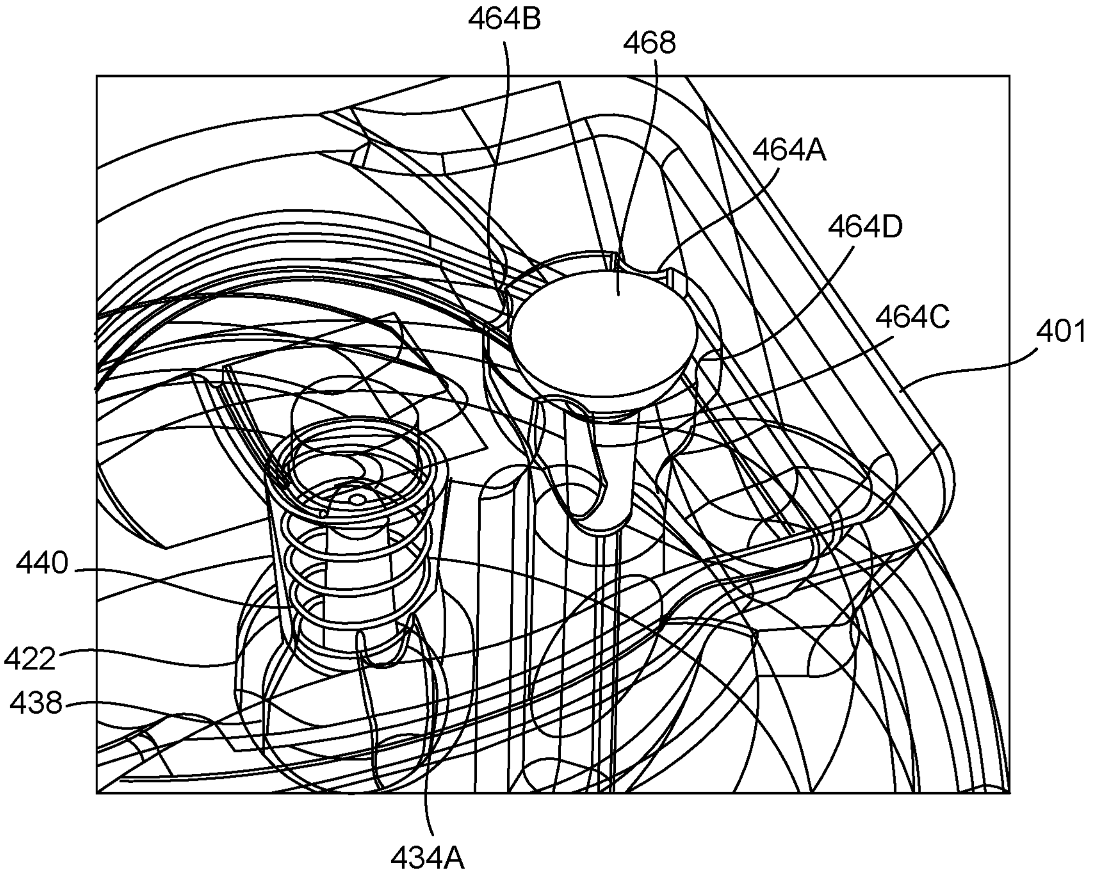

FIGS. 4A and 4B illustrate a portion of a pump assembly 401 according to an aspect. The pump assembly 401 can include any combination of features of the pump assembly 101, 201 described above.

A portion of a valve can include a tail 460. The tail 460 can include any combination of features of the tail 160 described above. The tail 460 can include and/or define multiple, such as four, guides 464A, 464B, 464C, 464D. The guides 464A, 464B, 464C, 464D can include any combination of features of the guides 164A, 164B, 164C, 164D described above. The guides 464A, 464B, 464C, 464D can extend toward a center of the tail 460.

The valve can include a poppet 468. The poppet 468 can include any combination of features of the poppet 168 described above. A stem of the poppet 468 can extend through an exit tube interface 466. The exit tube interface 466 can include any combination of features of the exit tube interface 166 described above. When fluid is flowing through the valve, the poppet 468 can rest against the guides 464A, 464B, 464C, 464D. With the poppet 468 resting against the guides 464A, 464B, 464C, 464D, fluid can still flow between the guides 464A, 464B, 464C, 464D and between the poppet 468 and the tail 460. The valve can include a biasing member biasing the poppet 468 away from the tail 460, shown in FIGS. 4A and 4B with respect to another tail 430.

A biasing member 440, such as a spring or coil, can bias a poppet 438 away from the tail 430 of a second valve. The biasing member 40 can include any combination of features described above with respect to the biasing member 170. The tail 430 can include any combination of features described above with respect to the tail 160, 460. The poppet 438 can include any combination of features described above with respect to the poppet 168, 468. The tail 430 can include and/or define multiple guides 434A (of which one guide 434A is shown in FIGS. 4A and 4B). The guides 434A can include any combination of features described above with respect to the guides 164A, 164B, 164C, 164D, 464A, 464B, 464C, 464D. The poppet 438 can be included in a bulb 422 of the valve. The bulb 422 can include any combination of features described above with respect to the bulb 452.

Figure 5:
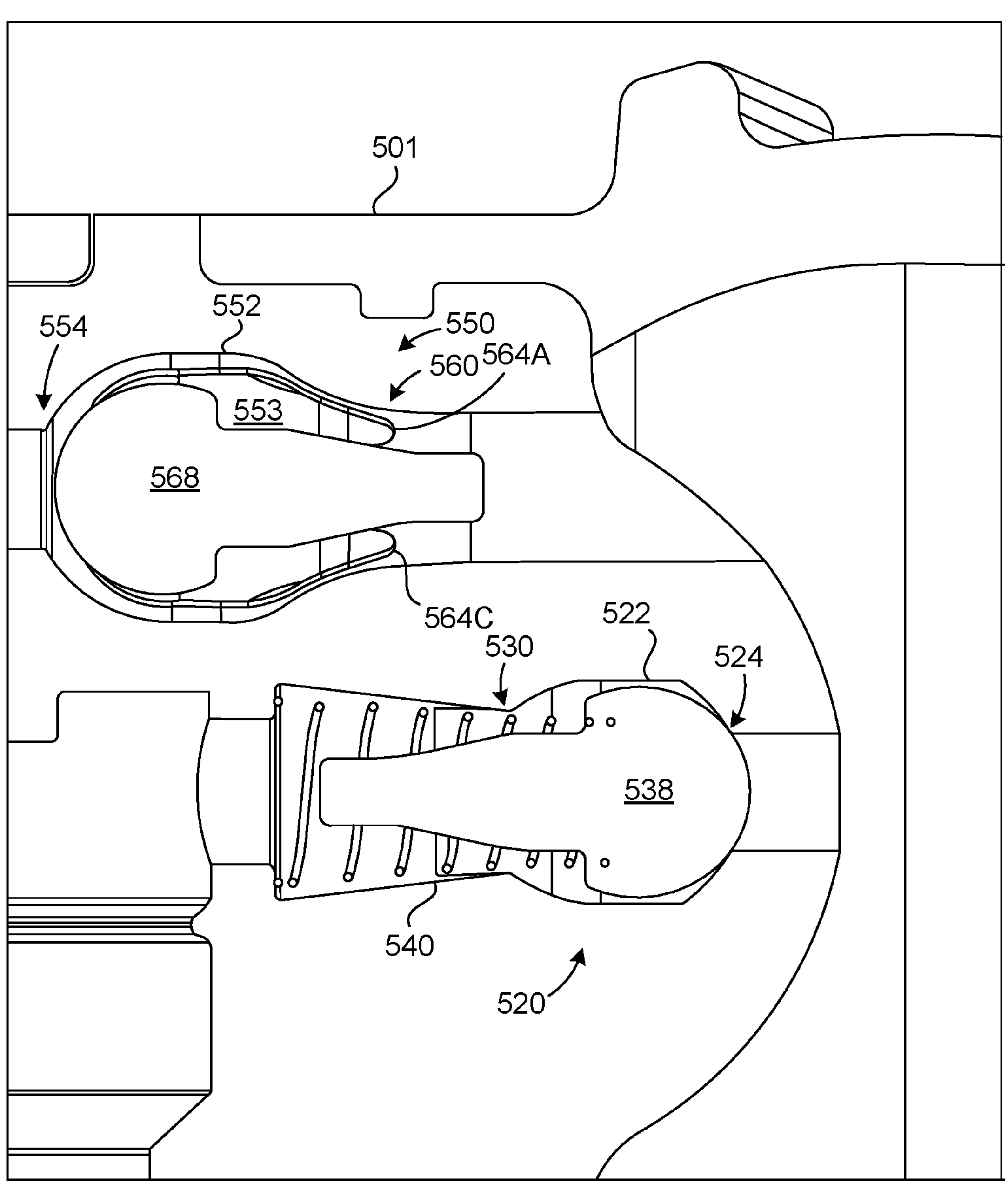
FIG. 5 illustrates a portion of a pump assembly according to another aspect.

FIG. 5 illustrates a portion of a pump assembly 501 according to another aspect. The pump assembly 501 can include two valves 520, 550. In some examples, the valve 520 is an example of a refill valve 108 and the valve 550 is an example of an inflation valve 110. In some examples, the valve 520 is an example of an inflation valve 110 and the valve 550 is an example of a refill valve 108.

The valves 520, 550 can include bulbs 522, 552 with any combination of features of the bulbs 152, 422 described above. The bulbs 522, 552 can each define a chamber 553 (not labeled with respect to the bulb 522). Poppets 538, 568 can be included in the chambers 553, and can include any combination of features of the poppets 168, 438, 468 described above. The valves 520, 550 can include bases 524, 554 with any combination of features of the base 154 described above. The valves 520, 550 can include tails 530, 560 with any combination of the tails 160, 460, 430 described above. The tails 530, 560 can include guides 564A, 564C (not labeled with respect to the tail 560) with any combination of features of the guides 164A, 164B, 164C, 164D, 464A, 464B, 464C, 464D, 434A described above. In some examples, the valve 550 can include a biasing member similar to the biasing member 540 shown in the valve 520. The biasing member 540 can include any combination of features of the biasing member 170, 440 described above.

In some examples, the poppet 538, 568 can be considered a guided comet valve. The poppet 538, 568 can include a spherical member, a cylindrical member extending from the spherical member, and a partial cone member extending from the spherical member. The partial cone member can extend through the tail 530, 560. This example of the poppet 538, 568 is described further with respect to FIGS. 13A and 13B.

Figure 6:
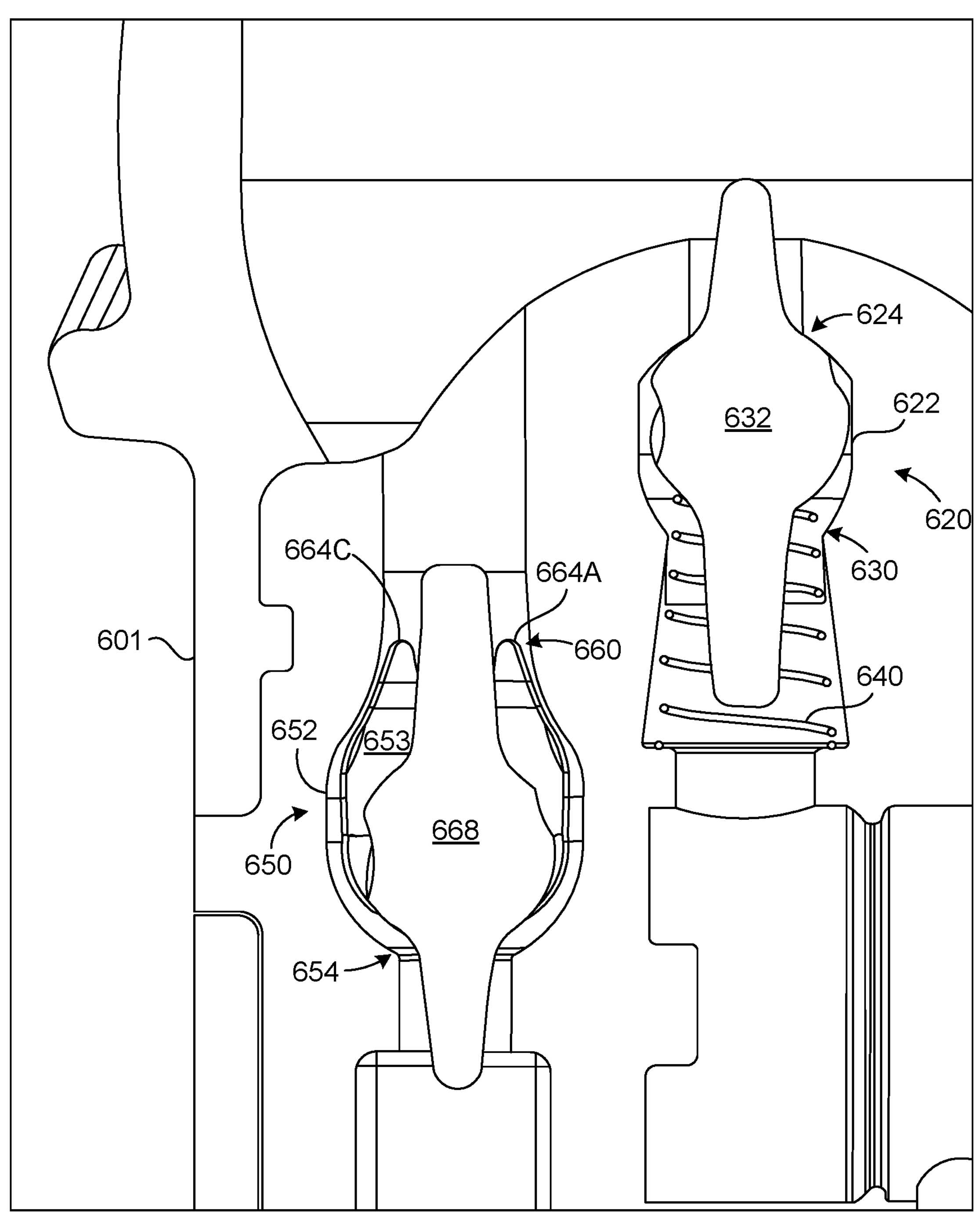
FIG. 6 illustrates a portion of a pump assembly according to another aspect.

FIG. 6 illustrates a portion of a pump assembly 601 according to another aspect. The pump assembly 601 can include two valves 620, 650. In some examples, the valve 620 is an example of a refill valve 108 and the valve 650 is an example of an inflation valve 110. In some examples, the valve 620 is an example of an inflation valve 110 and the valve 650 is an example of a refill valve 108.

The valves 620, 650 can include bulbs 622, 652 with any combination of features of the bulbs 152, 422, 522, 552 described above. The bulbs 622, 652 can each define a chamber 653 (not labeled with respect to the bulb 622). Poppets 638, 668 can be included in the chambers 653, and can include any combination of features of the poppets 168, 438, 468, 538, 568 described above. The valves 620, 650 can include bases 624, 654 with any combination of features of the bases 154, 524, 554 described above. The valves 620, 650 can include tails 630, 660 with any combination of the tails 160, 460, 430, 530, 560 described above. The tails 630, 660 can include guides 664A, 664C (not labeled with respect to the tail 630) with any combination of features of the guides 164A, 164B, 164C, 164D, 464A, 464B, 464C, 464D, 434A, 564A, 564C described above. In some examples, the valve 650 can include a biasing member similar to the biasing member 640 shown in the valve 620. The biasing member 640 can include any combination of features of the biasing member 170, 440, 540 described above.

In some examples, the poppet 638, 668 can be considered a guided vortex valve. The poppet 638, 668 can include a cap member with a rounded portion facing toward the base 654, 624 and defining multiple grooves, a base stem and/or entry portion stem extending from the rounded portion and through the base 624, 654, and an exit stem extending from a portion of the cap member opposite from the rounded portion and through the tail 630, 660. This example of the poppet 638, 668 is described further with respect to FIGS. 15A and 15B.

Figure 7:
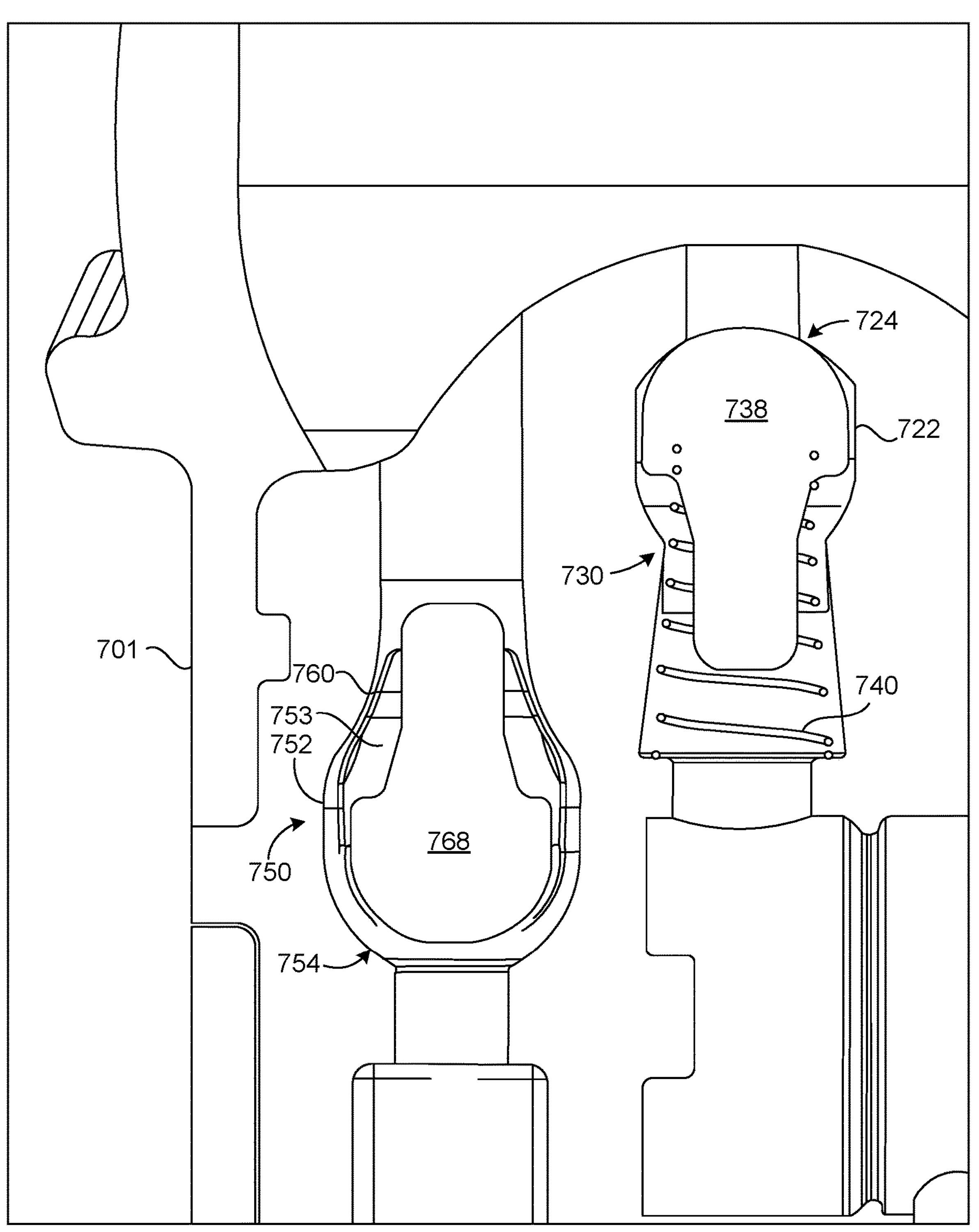
FIG. 7 illustrates a portion of a pump assembly according to another aspect.

FIG. 7 illustrates a portion of a pump assembly 701 according to another aspect. The pump assembly 701 can include two valves 720, 750. In some examples, the valve 720 is an example of a refill valve 108 and the valve 750 is an example of an inflation valve 110. In some examples, the valve 720 is an example of an inflation valve 110 and the valve 750 is an example of a refill valve 108.

The valves 720, 750 can include bulbs 722, 752 with any combination of features of the bulbs 152, 422, 522, 552, 622, 652 described above. The bulbs 722, 752 can each define a chamber 753 (not labeled with respect to the bulb 722). Poppets 738, 768 can be included in the chambers 753, and can include any combination of features of the poppets 168, 438, 468, 538, 568, 638, 668 described above. The valves 720, 750 can include bases 724, 754 with any combination of features of the bases 154, 524, 554, 624, 654 described above. The valves 720, 750 can include tails 730, 760 with any combination of the tails 160, 460, 430, 530, 560, 630, 660 described above. The tails 730, 760 can include guides (not labeled) with any combination of features of the guides 164A, 164B, 164C, 164D, 464A, 464B, 464C, 464D, 434A, 564A, 564C, 664A, 664C described above. In some examples, the valve 750 can include a biasing member similar to the biasing member 740 shown in the valve 720. The biasing member 740 can include any combination of features of the biasing member 170, 440, 540, 640 described above.

In some examples, the poppet 738, 768 can be considered a mushroom valve. The poppet 738, 768 can include a cap member and a stem. The cap member can have a semi-spherical shape and/or a rounded portion facing toward the base 754, 724 and a flat portion facing toward the tail 730, 760. The stem can extend from the flat portion of the cap member. This example of the poppet 738, 768 is described further with respect to FIGS. 12A and 12B.

Figure 8:
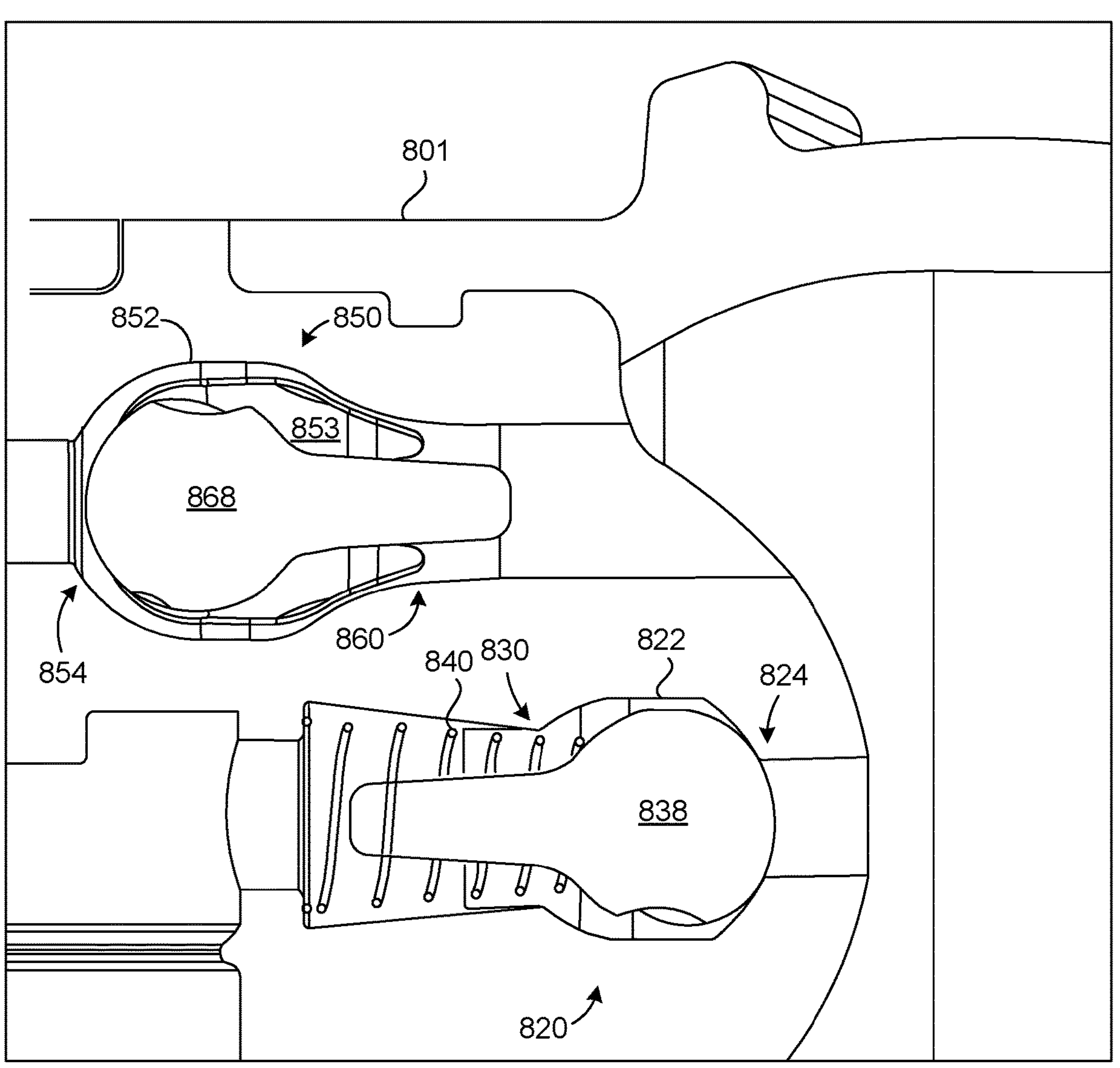
FIG. 8 illustrates a portion of a pump assembly according to another aspect.

FIG. 8 illustrates a portion of a pump assembly 801 according to another aspect. The pump assembly 801 can include two valves 820, 850. In some examples, the valve 820 is an example of a refill valve 108 and the valve 850 is an example of an inflation valve 110. In some examples, the valve 820 is an example of an inflation valve 110 and the valve 850 is an example of a refill valve 108.

The valves 820, 850 can include bulbs 822, 852 with any combination of features of the bulbs 152, 422, 522, 552, 622, 652, 722, 752 described above. The bulbs 822, 852 can each define a chamber 853 (not labeled with respect to the bulb 822). Poppets 838, 868 can be included in the chambers 853, and can include any combination of features of the poppets 168, 438, 468, 538, 568, 638, 668, 738, 768 described above. The valves 820, 850 can include bases 824, 854 with any combination of features of the bases 154, 524, 554, 624, 654, 724, 754 described above. The valves 820, 850 can include tails 830, 860 with any combination of the tails 160, 460, 430, 530, 560, 630, 660, 730, 760 described above. The tails 830, 860 can include guides (not labeled) with any combination of features of the guides 164A, 164B, 164C, 164D, 464A, 464B, 464C, 464D, 434A, 564A, 564C, 664A, 664C described above. In some examples, the valve 850 can include a biasing member similar to the biasing member 840 shown in the valve 820. The biasing member 840 can include any combination of features of the biasing member 170, 440, 540, 640, 740 described above.

In some examples, the poppet 838, 868 can be considered a vortex valve. The poppet 838, 868 can include a cap member and a stem. The cap member can include a rounded portion facing toward the base 824, 854, and can define multiple grooves. The grooves can be at equal intervals from each other and can extend in directions offset between thirty degrees (30°) and sixty degrees (60°) from each other. The stem can extend from a portion of the cap member opposite from the base 824, 854 through the tail 830, 860.

Figure 9:
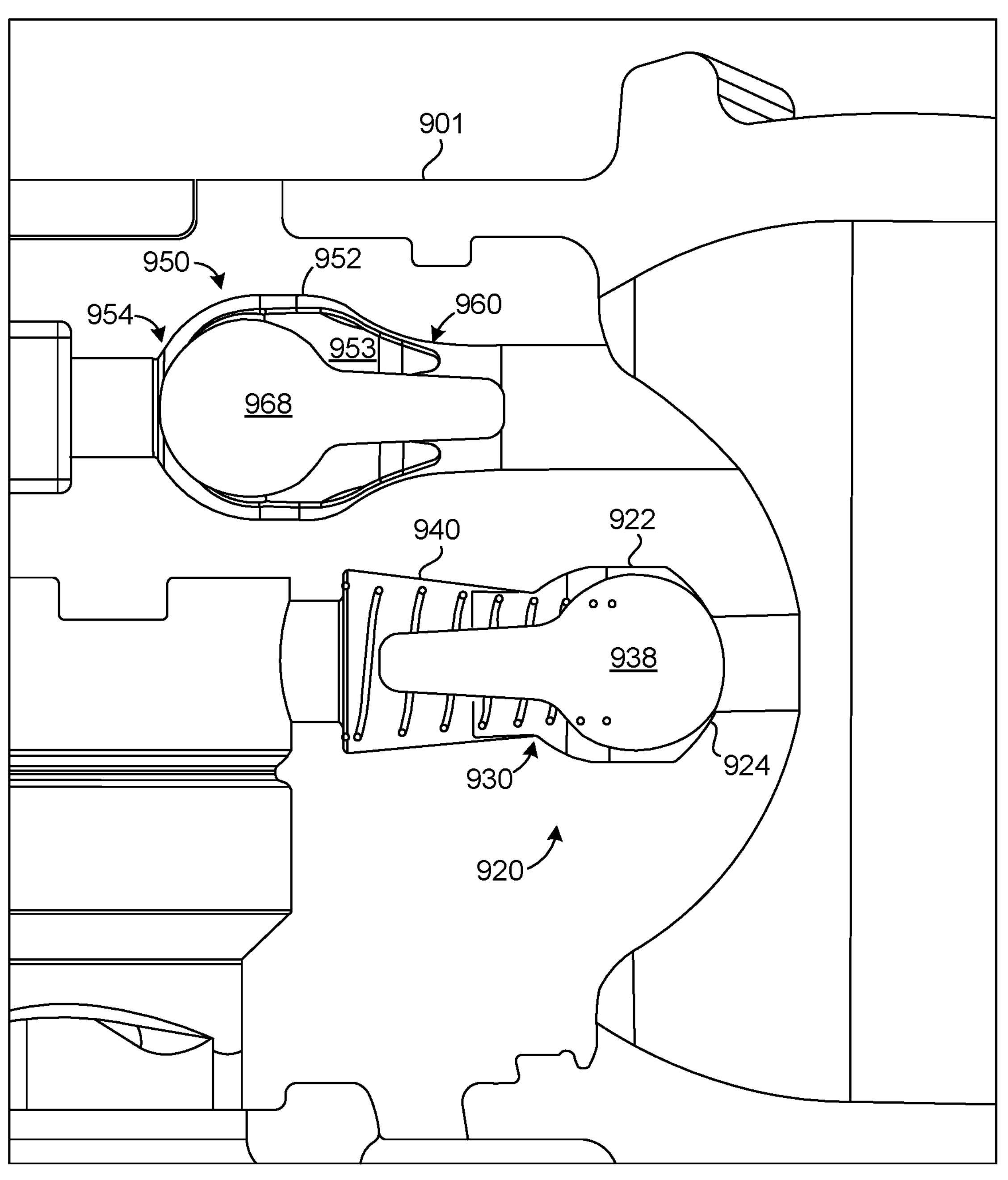
FIG. 9 illustrates a portion of a pump assembly according to another aspect.

FIG. 9 illustrates a portion of a pump assembly 901 according to another aspect. The pump assembly 901 can include two valves 920, 950. In some examples, the valve 920 is an example of a refill valve 108 and the valve 950 is an example of an inflation valve 110. In some examples, the valve 920 is an example of an inflation valve 110 and the valve 950 is an example of a refill valve 108.

The valves 920, 950 can include bulbs 922, 952 with any combination of features of the bulbs 152, 422, 522, 552, 622, 652, 722, 752, 822, 852 described above. The bulbs 922, 952 can each define a chamber 953 (not labeled with respect to the bulb 922). Poppets 938, 968 can be included in the chambers 953, and can include any combination of features of the poppets 168, 438, 468, 538, 568, 638, 668, 738, 768, 838, 868 described above. The valves 920, 950 can include bases 924, 954 with any combination of features of the bases 154, 524, 554, 624, 654, 724, 754, 824, 854 described above. The valves 920, 950 can include tails 930, 960 with any combination of the tails 160, 460, 430, 530, 560, 630, 660, 730, 760, 830, 860 described above. The tails 930, 960 can include guides (not labeled) with any combination of features of the guides 164A, 164B, 164C, 164D, 464A, 464B, 464C, 464D, 434A, 564A, 564C, 664A, 664C described above. In some examples, the valve 950 can include a biasing member similar to the biasing member 940 shown in the valve 920. The biasing member 940 can include any combination of features of the biasing member 170, 440, 540, 640, 740, 840 described above.

In some examples, the poppet 938, 968 can be considered a comet valve. The poppet 938, 968 can include a spherical member and a partial cone member extending from the spherical member. The partial cone member can extend through the tail 930, 960.

Figure 10A:
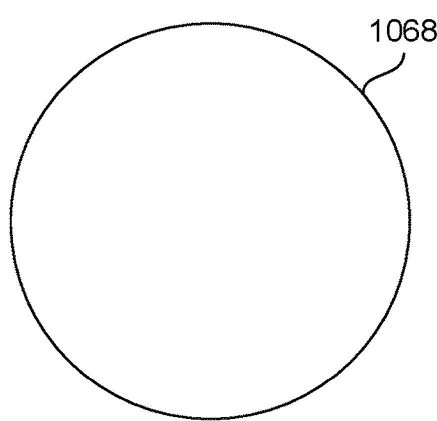
FIG. 10A illustrates a poppet that can be included in a valve according to an aspect.

FIG. 10A illustrates a poppet 1068 that can be included in a valve 150 according to an aspect. In this example, the poppet 1068 can be considered a simple ball valve. The poppet 1068 can be spherical, spherically shaped, and/or sphere shaped.

Figure 10B:
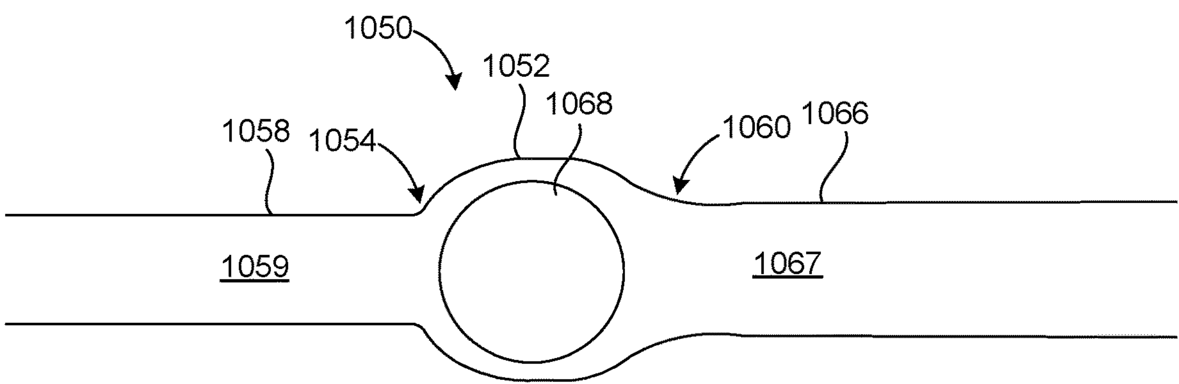
FIG. 10B illustrates a valve that includes the poppet of FIG. 10A according to an aspect.

FIG. 10B illustrates a valve 1050 that includes the poppet 1068 of FIG. 10A according to an aspect. The valve 1050 can include any combination of features of the valve 150 described above. The valve 1050 can be an example of a refill valve 108 or an inflation valve 110.

The valve 1050 can include an entry tube interface 1058. The entry tube interface 1058 can be configured to attach to an entry tube (which can include either of the conduit connectors 103, 105). The entry tube interface 1058 can define an entry passageway 1059 through which fluid flows into the valve 1050. The entry tube interface 1058 can include any combination of features of the entry tube interface 158 described above.

The valve 1050 can include a base 1054. The base 1054 can be adjacent to the entry tube interface 1058. The base 1054 can be circular about a longitudinal base axis (not shown in FIG. 10B). The longitudinal base axis can be parallel to a direction from which the entry tube interface 1058 extends from the base 1054. The base 1054 can define a base passageway (not labeled in FIG. 10B). The base 1054 can include any combination of features of the bases 154, 524, 554, 624, 654, 724, 754, 824, 854 924, 954 described above.

The valve 1050 can include a bulb 1052. The bulb 1052 can be adjacent to the base 1054. The bulb 1052 can be wider than the base 1054. The bulb 1052 can define a chamber (not labeled in FIG. 10B). The bulb 1052 can include any combination of features of the bulbs 152, 422, 522, 552, 622, 652, 722, 752, 822, 852, 922, 952 described above.

The poppet 1068 can be disposed inside the chamber defined by the bulb 1052. The poppet 1068 can be biased to rest against the base 1054. When the poppet 1068 is resting against the base 1054, the valve 1050 can be sealed, preventing fluid from flowing through the valve 1050. While not shown in FIG. 10B, the valve 1050 can include a biasing member, such as a spring, biasing the poppet 1068 to rest against the base 1054. The biasing member can include any combination of features of the biasing members 170, 440, 540, 640, 740, 840, 940 described above.

The valve 1050 can include a tail 1060. The tail 1060 can be adjacent to the bulb 1052. The tail 1060 can be narrower than the bulb 1052. The tail 1060 can define a tail passageway (not labeled in FIG. 10B). The tail 1060 can include and/or define multiple guides (not labeled in FIG. 10B). The multiple guides can extend toward a longitudinal exit axis (not shown in FIG. 10B). The longitudinal exit axis can extend through a center of the tail 1060 parallel to a direction that an exit tube interface 1066 extends from the tail 1060. The multiple guides can be symmetrical about the longitudinal exit axis. The tail 1060 can include any combination of features of the tails 160, 460, 430, 530, 560, 630, 660, 730, 760, 830, 860 described above.

The valve 1050 can include the exit tube interface 1066. The exit tube interface 1066 can be adjacent to the tail 1060. The exit tube interface 1066 can be configured to attach to an exit tube (which can include either of the conduit connectors 103, 105). The exit tube interface 1066 can define an exit passageway 1067 through which fluid flows out of the valve 1050. The exit tube interface 1066 can include any combination of features of the exit tube interfaces 166, 466 described above.

During high flow conditions into the entry tube interface 1058, pressure against the poppet 1068 can overcome the biasing force on the poppet 1068, and/or cause the poppet 1068 to rest against the guides in the open position. The friction caused by the contact of the poppet 1068 against the guides can prevent the poppet 1068 from rotating and/or oscillating within the chamber defined by the bulb 1052, preventing noise and/or causing the valve to become silent during the high flow conditions.

Figure 11A:
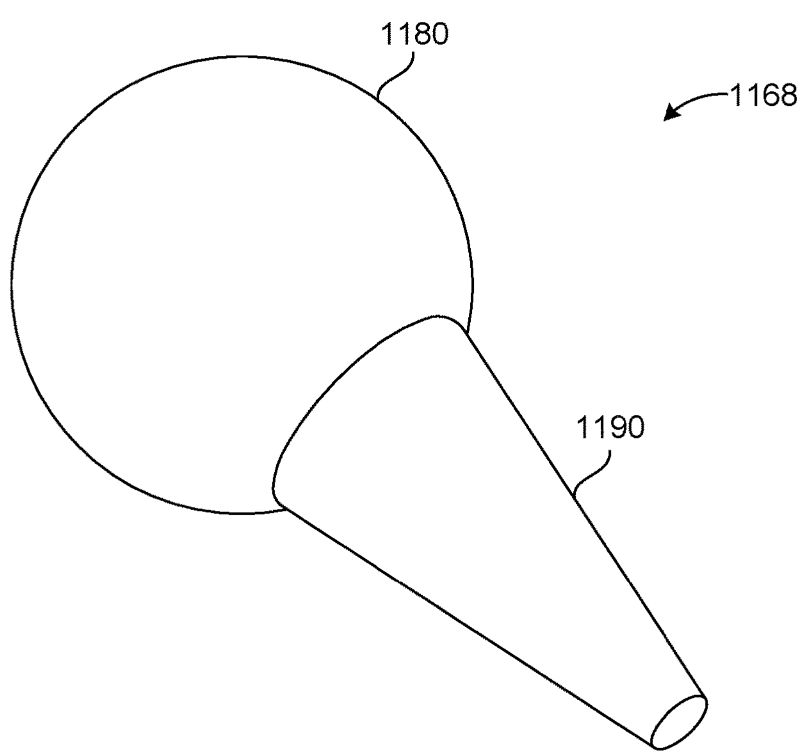
FIG. 11A illustrates a poppet that can be included in a valve according to an aspect.

FIG. 11A illustrates a poppet 1168 that can be included in a valve according to an aspect. In this example, the poppet 1168 can be considered a comet valve. The poppet 1168 can include a spherical member 1180, semispherical member, and/or a semispherical nose, and a partial cone member 1190 extending from the spherical member 1180 and/or semispherical nose.

Figure 11B:
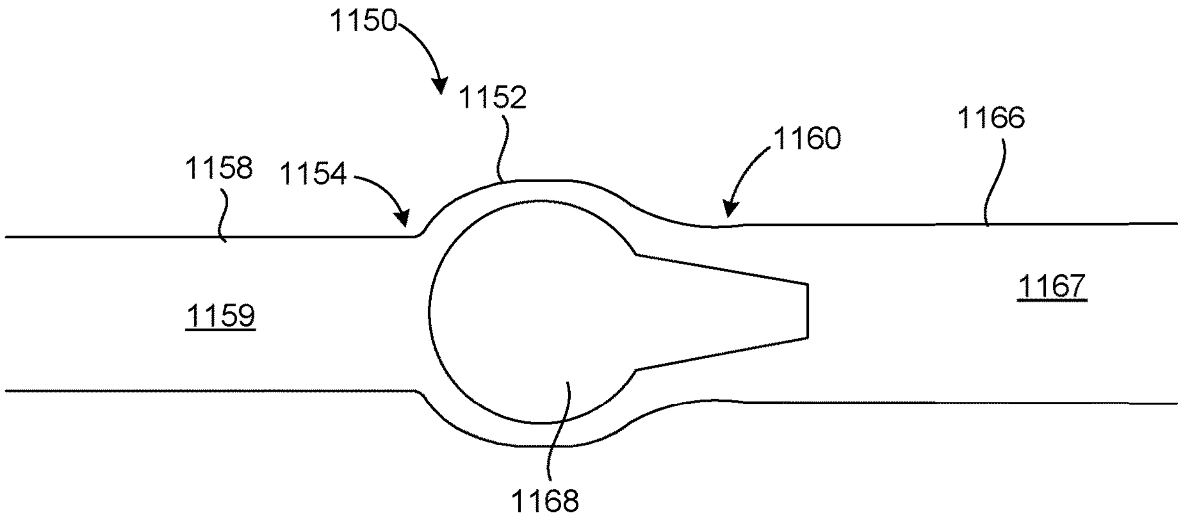
FIG. 11B illustrates a valve that includes the poppet of FIG. 11A according to an aspect.

FIG. 11B illustrates a valve 1150 that includes the poppet 1168 of FIG. 11A according to an aspect. The valve 1150 can include any combination of features of the valves 150, 1050 described above. The valve 1150 can be an example of a refill valve 108 or an inflation valve 110.

The valve 1150 can include an entry tube interface 1158. The entry tube interface 1158 can be configured to attach to an entry tube (which can include either of the conduit connectors 103, 105). The entry tube interface 1158 can define an entry passageway 1159 through which fluid flows into the valve 1150. The entry tube interface 1158 can include any combination of features of the entry tube interface 158, 1058 described above.

The valve 1150 can include a base 1154. The base 1154 can be adjacent to the entry tube interface 1158. The base 1154 can be circular about a longitudinal base axis (not shown in FIG. 11B). The longitudinal base axis can be parallel to a direction from which the entry tube interface 1158 extends from the base 1154. The base 1154 can define a base passageway (not labeled in FIG. 11B). The base 1154 can include any combination of features of the bases 154, 524, 554, 624, 654, 724, 754, 824, 854 924, 954, 1054 described above.

The valve 1150 can include a bulb 1152. The bulb 1152 can be adjacent to the base 1154. The bulb 1152 can be wider than the base 1154. The bulb 1152 can define a chamber (not labeled in FIG. 11B). The bulb 1152 can include any combination of features of the bulbs 152, 422, 522, 552, 622, 652, 722, 752, 822, 852, 922, 952, 1052 described above.

The poppet 1168 can be disposed inside the chamber defined by the bulb 1152. The poppet 1168 can be biased to rest against the base 1154. When the spherical member 1180 of the poppet 1168 is resting against the base 1154, the valve 1150 can be sealed, preventing fluid from flowing through the valve 1150. While not shown in FIG. 11B, the valve 1150 can include a biasing member, such as a spring, biasing the poppet 1168 to rest against the base 1154. The biasing member can include any combination of features of the biasing members 170, 440, 540, 640, 740, 840, 940 described above.

The valve 1150 can include a tail 1160. The tail 1160 can be adjacent to the bulb 1152. The tail 1160 can be narrower than the bulb 1152. The tail 1160 can define a tail passageway (not labeled in FIG. 11B). The tail 1160 can include and/or define multiple guides (not labeled in FIG. 11B). The multiple guides can extend toward a longitudinal exit axis (not shown in FIG. 11B). The longitudinal exit axis can extend through a center of the tail 1160 parallel to a direction that an exit tube interface 1166 extends from the tail 1160. The multiple guides can be symmetrical about the longitudinal exit axis. The tail 1160 can include any combination of features of the tails 160, 460, 430, 530, 560, 630, 660, 730, 760, 830, 860, 1060 described above.

The valve 1150 can include the exit tube interface 1166. The exit tube interface 1166 can be adjacent to the tail 1160. The exit tube interface 1166 can be configured to attach to an exit tube (which can include either of the conduit connectors 103, 105). The exit tube interface 1166 can define an exit passageway 1167 through which fluid flows out of the valve 1150. The exit tube interface 1166 can include any combination of features of the exit tube interfaces 166, 466, 1066 described above.

During high flow conditions into the entry tube interface 1158, pressure against the spherical member 1180 can overcome the biasing force on the poppet 1168, and/or cause the poppet 1168 to rest against the guides in the open position. During the high flow conditions, the partial cone member 1190 can extend through the tail passageway defined by the tail 1160 and into the exit passageway 1167. The partial cone member 1190 can reduce a pressure drop across a side of the spherical member 1180 opposite from the base 1154, decreasing turbulent flow. The partial cone member 1190 can also stabilize the poppet 1168, isolating vibrations and preventing noise.

Figure 12A:
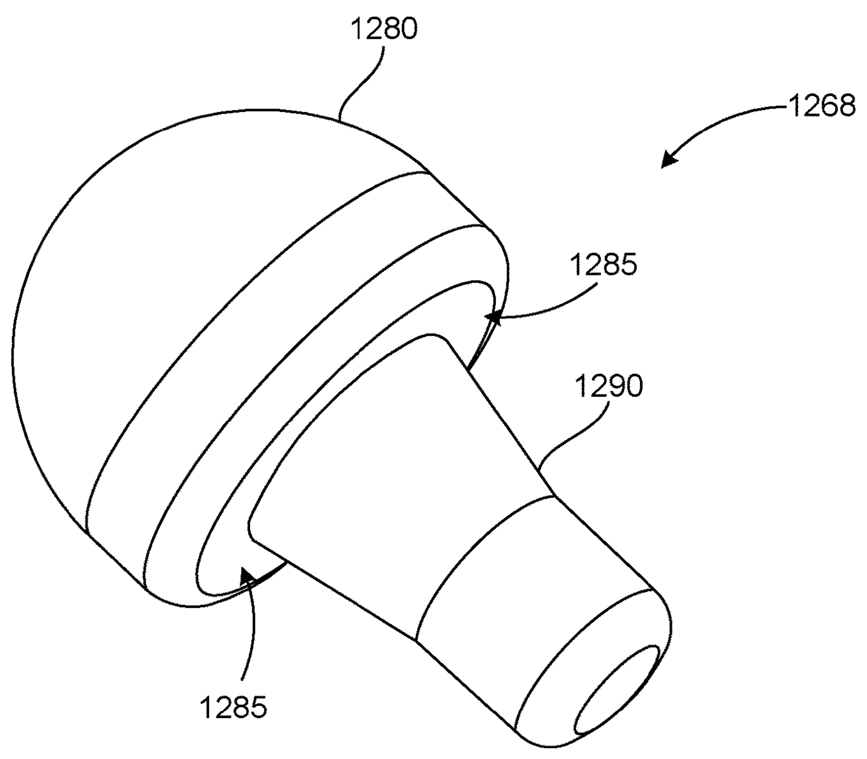
FIG. 12A illustrates a poppet that can be included in a valve according to an aspect.

FIG. 12A illustrates a poppet 1268 that can be included in a valve according to an aspect. In this example, the poppet 1268 can be considered a mushroom valve. The poppet 1268 can include a cap member. The cap member can include a rounded portion 1280 that faces toward a base 1254 (shown in FIG. 12B) and a flat portion 1285 facing toward a tail 1260 (shown in FIG. 12B). The poppet 1268 can include a stem 1290 extending from the flat portion 1285 of the cap member. A widest portion of the stem 1290 can be adjacent to the flat portion 1285 of the cap member. The stem 1290 can extend through a tail passageway defined by the tail and into an exit passageway 1267 (shown in FIG. 12B).

Figure 12B:
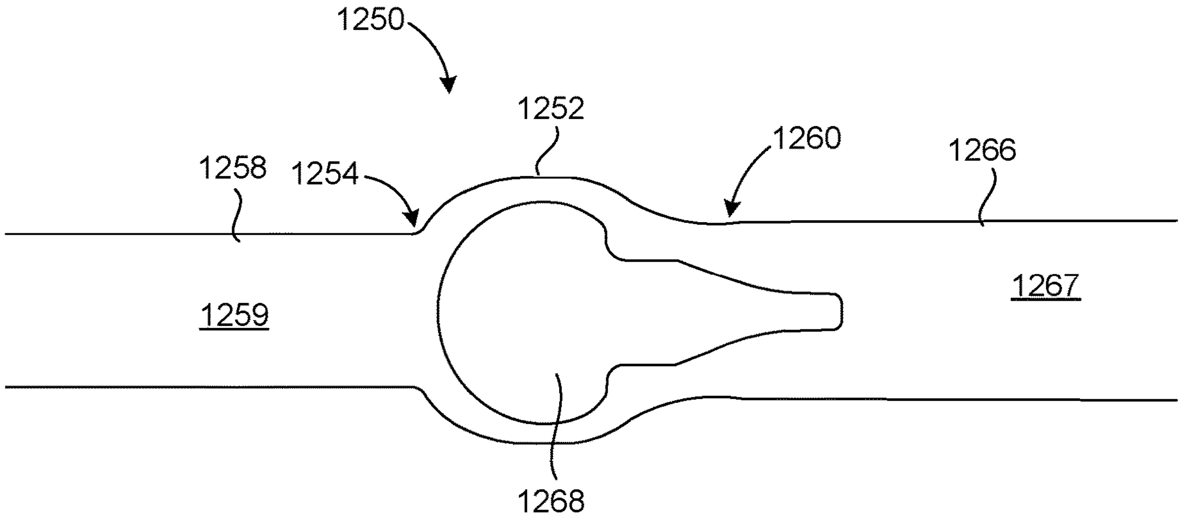
FIG. 12B illustrates a valve that includes the poppet of FIG. 12A according to an aspect.

FIG. 12B illustrates a valve 1250 that includes the poppet of FIG. 12A according to an aspect. The valve 1250 can include any combination of features of the valves 150, 1050, 1150 described above. The valve 1250 can be an example of a refill valve 108 or an inflation valve 110.

The valve 1250 can include an entry tube interface 1258. The entry tube interface 1258 can be configured to attach to an entry tube (which can include either of the conduit connectors 103, 105). The entry tube interface 1258 can define an entry passageway 1259 through which fluid flows into the valve 1250. The entry tube interface 1258 can include any combination of features of the entry tube interface 158, 1058, 1158 described above.

The valve 1250 can include a base 1254. The base 1254 can be adjacent to the entry tube interface 1258. The base 1254 can be circular about a longitudinal base axis (not shown in FIG. 12B). The longitudinal base axis can be parallel to a direction from which the entry tube interface 1258 extends from the base 1254. The base 1254 can define a base passageway (not labeled in FIG. 12B). The base 1254 can include any combination of features of the bases 154, 524, 554, 624, 654, 724, 754, 824, 854 924, 954, 1054, 1154 described above.

The valve 1250 can include a bulb 1252. The bulb 1252 can be adjacent to the base 1254. The bulb 1252 can be wider than the base 1254. The bulb 1252 can define a chamber (not labeled in FIG. 12B). The bulb 1252 can include any combination of features of the bulbs 152, 422, 522, 552, 622, 652, 722, 752, 822, 852, 922, 952, 1052, 1152 described above.

The poppet 1268 can be disposed inside the chamber defined by the bulb 1252. The poppet 1268 can be biased to rest against the base 1254. When the rounded portion 1280 of the cap member of the poppet 1268 is resting against the base 1254, the valve 1250 can be sealed, preventing fluid from flowing through the valve 1250. While not shown in FIG. 12B, the valve 1250 can include a biasing member, such as a spring, biasing the poppet 1268 to rest against the base 1254. The biasing member can include any combination of features of the biasing members 170, 440, 540, 640, 740, 840, 940 described above.

The valve 1250 can include a tail 1260. The tail 1260 can be adjacent to the bulb 1252. The tail 1260 can be narrower than the bulb 1252. The tail 1260 can define a tail passageway (not labeled in FIG. 12B). The tail 1260 can include and/or define multiple guides (not labeled in FIG. 12B). The multiple guides can extend toward a longitudinal exit axis (not shown in FIG. 12B). The longitudinal exit axis can extend through a center of the tail 1260 parallel to a direction that an exit tube interface 1266 extends from the tail 1260. The multiple guides can be symmetrical about the longitudinal exit axis. The tail 1260 can include any combination of features of the tails 160, 460, 430, 530, 560, 630, 660, 730, 760, 830, 860, 1060, 1160 described above.

The valve 1250 can include the exit tube interface 1266. The exit tube interface 1266 can be adjacent to the tail 1260. The exit tube interface 1266 can be configured to attach to an exit tube (which can include either of the conduit connectors 103, 105). The exit tube interface 1266 can define an exit passageway 1267 through which fluid flows out of the valve 1250. The exit tube interface 1266 can include any combination of features of the exit tube interfaces 166, 466, 1066, 1166 described above.

During high flow conditions into the entry tube interface 1258, pressure against the cap member can overcome the biasing force on the poppet 1268, and/or cause the flat portion 1285 of the poppet 1268 to rest against the guides in the open position. During the high flow conditions, the stem 1290 can extend through the tail passageway defined by the tail 1260 and into the exit passageway 1267. The stem 1290 can reduce a pressure drop across the cap member, decreasing turbulent flow. The generally cylindrical shape of the stem 1290 can also stabilize and align the poppet 1268 with the guides, isolating vibrations and preventing noise.

Figure 13A:
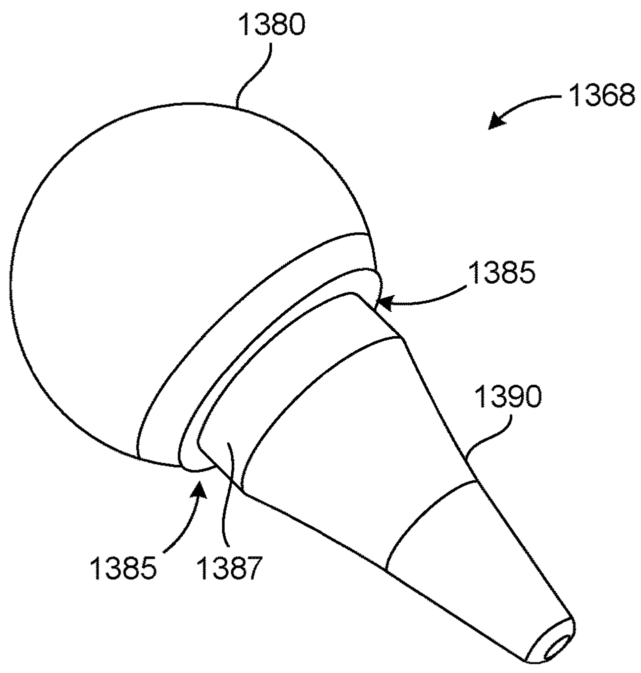
FIG. 13A illustrates a poppet that can be included in a valve according to an aspect.

FIG. 13A illustrates a poppet 1368 that can be included in a valve according to an aspect. In this example, the poppet 1368 can be considered a guide comet valve. In this example, the poppet 1368 includes a semispherical member

1380 with a flat portion 1385, a cylindrical member 1387 extending from the flat portion 1385 of the semispherical member 1380, and a partial cone member 1390 extending from the cylindrical member 1387. The partial cone member 1390 can extend through a tail passageway defined by a tail 1360 (shown in FIG. 13B) and into an exit passageway 1367 (shown in FIG. 13B).

Figure 13B:
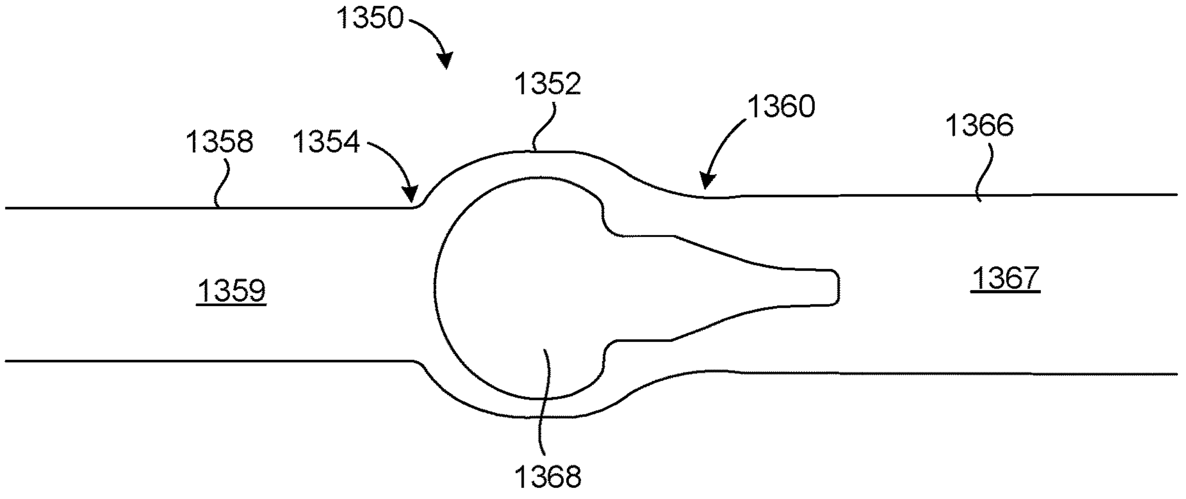
FIG. 13B illustrates a valve that includes the poppet of FIG. 13A according to an aspect.

FIG. 13B illustrates a valve 1350 that includes the poppet 1368 of FIG. 13A according to an aspect. The valve 1350 can include any combination of features of the valves 150, 1050, 1150, 1250 described above. The valve 1350 can be an example of a refill valve 108 or an inflation valve 110.

The valve 1350 can include an entry tube interface 1358. The entry tube interface 1358 can be configured to attach to an entry tube (which can include either of the conduit connectors 103, 105). The entry tube interface 1358 can define an entry passageway 1359 through which fluid flows into the valve 1350. The entry tube interface 1358 can include any combination of features of the entry tube interface 158, 1058, 1158, 1258 described above.

The valve 1350 can include a base 1354. The base 1354 can be adjacent to the entry tube interface 1358. The base 1354 can be circular about a longitudinal base axis (not shown in FIG. 13B). The longitudinal base axis can be parallel to a direction from which the entry tube interface 1358 extends from the base 1354. The base 1354 can define a base passageway (not labeled in FIG. 13B). The base 1354 can include any combination of features of the bases 154, 524, 554, 624, 654, 724, 754, 824, 854 924, 954, 1054, 1154, 1254 described above.

The valve 1350 can include a bulb 1352. The bulb 1352 can be adjacent to the base 1354. The bulb 1352 can be wider than the base 1354. The bulb 1352 can define a chamber (not labeled in FIG. 13B). The bulb 1352 can include any combination of features of the bulbs 152, 422, 522, 552, 622, 652, 722, 752, 822, 852, 922, 952, 1052, 1152, 1252 described above.

The poppet 1368 can be disposed inside the chamber defined by the bulb 1352. The semispherical member 1380 of the poppet 1368 can be biased to rest against the base 1354. When the semispherical member 1380 of the poppet 1368 is resting against the base 1354, the valve 1350 can be sealed, preventing fluid from flowing through the valve 1350. While not shown in FIG. 13B, the valve 1350 can include a biasing member, such as a spring, biasing the semispherical member 1380 of the poppet 1368 to rest against the base 1354. The biasing member can include any combination of features of the biasing members 170, 440, 540, 640, 740, 840, 940 described above.

The valve 1350 can include a tail 1360. The tail 1360 can be adjacent to the bulb 1352. The tail 1360 can be narrower than the bulb 1352. The tail 1360 can define a tail passageway (not labeled in FIG. 13B). The tail 1360 can include and/or define multiple guides (not labeled in FIG. 13B). The multiple guides can extend toward a longitudinal exit axis (not shown in FIG. 13B). The longitudinal exit axis can extend through a center of the tail 1360 parallel to a direction that an exit tube interface 1366 extends from the tail 1360. The multiple guides can be symmetrical about the longitudinal exit axis. The tail 1360 can include any combination of features of the tails 160, 460, 430, 530, 560, 630, 660, 730, 760, 830, 860, 1060, 1160, 1260 described above.

The valve 1350 can include the exit tube interface 1366. The exit tube interface 1366 can be adjacent to the tail 1360. The exit tube interface 1366 can be configured to attach to an exit tube (which can include either of the conduit connectors 103, 105). The exit tube interface 1366 can define an exit passageway 1367 through which fluid flows out of the valve 1350. The exit tube interface 1366 can include any combination of features of the exit tube interfaces 166, 466, 1066, 1166, 1266 described above.

During high flow conditions into the entry tube interface 1358, pressure against the semispherical member 1380 can overcome the biasing force on the poppet 1368, and/or cause the flat portion 1385 of the poppet 1368 to rest against the guides in the open position. During the high flow conditions, the partial cone member 1390 can extend through the tail passageway defined by the tail 1360 and into the exit passageway 1367. The partial cone member 1390 can reduce a pressure drop across the semispherical member 1380, decreasing turbulent flow. The partial cone member 1390 can also stabilize and align the poppet 1368 with the guides, isolating vibrations and preventing noise.

Figure 14A:
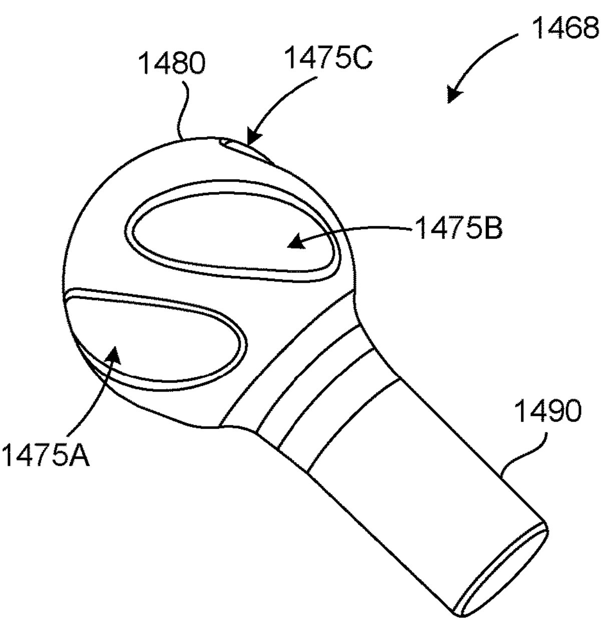
FIG. 14A illustrates a poppet that can be included in a valve according to an aspect.

FIG. 14A illustrates a poppet 1468 that can be included in a valve according to an aspect. The poppet 1468 can be considered a vortex valve. The poppet 1468 can include a cap member 1480 and a stem 1490. The cap member 1480 can include a rounded portion facing toward a base 1454 (shown in FIG. 14B). The cap member 1480 can include multiple, such as four, grooves 1475A, 1475B, 1475C. The grooves 1475A, 1475B, 1475C can be spaced at equal intervals from each other. The grooves 1475A, 1475B, 1475C can extend in directions offset between thirty degrees (30°) and sixty degrees (60°) from a direction that the stem 1490 extends from the cap member 1480. The stem 1490 can extend from a portion of the cap member 1480 opposite from the rounded portion, through a tail passageway defined by a tail 1460 (shown in FIG. 14B), and into an exit passageway 1467 (shown in FIG. 14B).

Figure 14B:
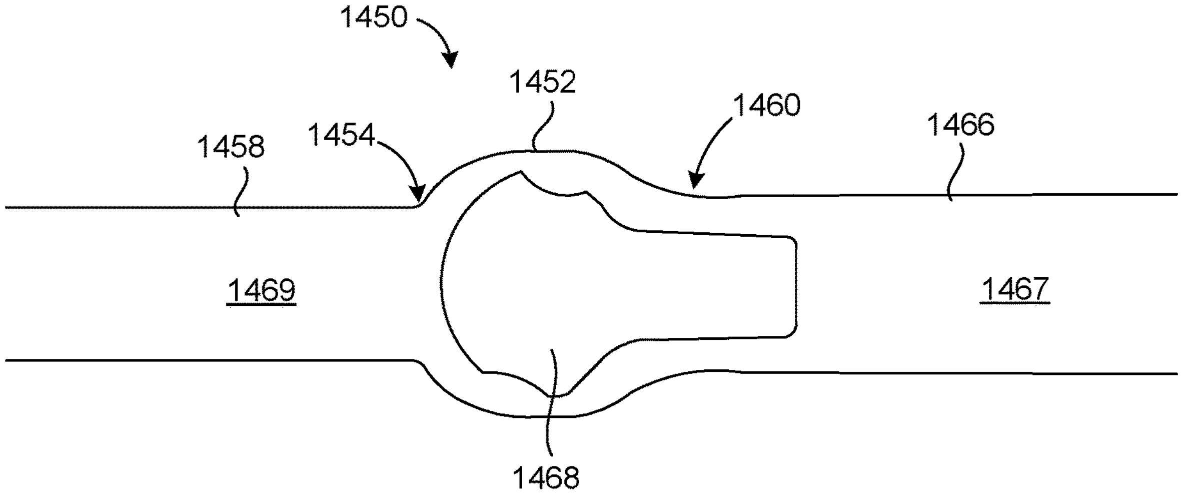
FIG. 14B illustrates a valve that includes the poppet of FIG. 14A according to an aspect.

FIG. 14B illustrates a valve 1450 that includes the poppet 1468 of FIG. 14A according to an aspect. The valve 1450 can include any combination of features of the valves 150, 1050, 1150, 1250, 1350 described above. The valve 1450 can be an example of a refill valve 108 or an inflation valve 110.

The valve 1450 can include an entry tube interface 1458. The entry tube interface 1458 can be configured to attach to an entry tube (which can include either of the conduit connectors 103, 105). The entry tube interface 1458 can define an entry passageway 1459 through which fluid flows into the valve 1450. The entry tube interface 1458 can include any combination of features of the entry tube interface 158, 1058, 1158, 1258, 1358 described above.

The valve 1450 can include a base 1454. The base 1454 can be adjacent to the entry tube interface 1458. The base 1454 can be circular about a longitudinal base axis (not shown in FIG. 14B). The longitudinal base axis can be parallel to a direction from which the entry tube interface 1458 extends from the base 1454. The base 1454 can define a base passageway (not labeled in FIG. 14B). The base 1454 can include any combination of features of the bases 154, 524, 554, 624, 654, 724, 754, 824, 854 924, 954, 1054, 1154, 1254, 1354 described above.

The valve 1450 can include a bulb 1452. The bulb 1452 can be adjacent to the base 1454. The bulb 1452 can be wider than the base 1454. The bulb 1452 can define a chamber (not labeled in FIG. 14B). The bulb 1452 can include any combination of features of the bulbs 152, 422, 522, 552, 622, 652, 722, 752, 822, 852, 922, 952, 1052, 1152, 1252, 1352 described above.

The poppet 1468 can be disposed inside the chamber defined by the bulb 1452. The rounded portion of the cap member 1480 of the poppet 1468 can be biased to rest against the base 1454. When the rounded portion of the cap member 1480 of the poppet 1468 is resting against the base 1454, the valve 1450 can be sealed, preventing fluid from flowing through the valve 1450. While not shown in FIG. 14B, the valve 1450 can include a biasing member, such as a spring, biasing the semispherical cap member 1480 of the poppet 1468 to rest against the base 1454. The biasing member can include any combination of features of the biasing members 170, 440, 540, 640, 740, 840, 940 described above.

The valve 1450 can include a tail 1460. The tail 1460 can be adjacent to the bulb 1452. The tail 1460 can be narrower than the bulb 1452. The tail 1460 can define a tail passageway (not labeled in FIG. 14B). The tail 1460 can include and/or define multiple guides (not labeled in FIG. 14B). The multiple guides can extend toward a longitudinal exit axis (not shown in FIG. 14B). The longitudinal exit axis can extend through a center of the tail 1460 parallel to a direction that an exit tube interface 1466 extends from the tail 1460. The multiple guides can be symmetrical about the longitudinal exit axis. The tail 1460 can include any combination of features of the tails 160, 460, 430, 530, 560, 630, 660, 730, 760, 830, 860, 1060, 1160, 1260, 1360 described above.

The valve 1450 can include the exit tube interface 1466. The exit tube interface 1466 can be adjacent to the tail 1460. The exit tube interface 1466 can be configured to attach to an exit tube (which can include either of the conduit connectors 103, 105). The exit tube interface 1466 can define an exit passageway 1467 through which fluid flows out of the valve 1450. The exit tube interface 1466 can include any combination of features of the exit tube interfaces 166, 466, 1066, 1166, 1266, 1366 described above.

During high flow conditions into the entry tube interface 1458, pressure against the cap member 1480 can overcome the biasing force on the poppet 1468, and/or cause the portion of the poppet 1468 opposite from the rounded portion that rests against the base 1454 to rest against the guides in the open position. During the high flow conditions, the stem 1490 can extend through the tail passageway defined by the tail 1460 and into the exit passageway 1467. The stem 1490 can reduce a pressure drop across the cap member 1480, decreasing turbulent flow. The stem 1490 can also stabilize and align the poppet 1468 with the guides, isolating vibrations and preventing noise. The grooves 1475A, 1475B, 1475C can form a helix, forcing the poppet 1468 to rotate, which improves axial alignment of the stem 1490 and stabilizes the poppet 1468, reducing noise.

Figure 15A:
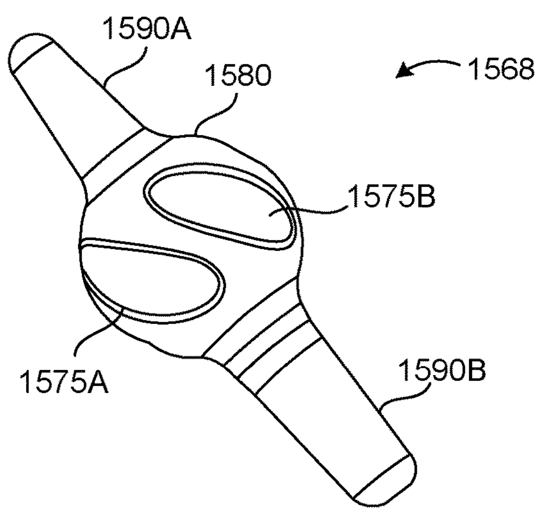
FIG. 15A illustrates a poppet that can be included in a valve according to an aspect.

FIG. 15A illustrates a poppet 1568 that can be included in a valve according to an aspect. The poppet 1568 can be considered a guided vortex valve. The poppet 1568 can include a cap member 1580, a base stem 1590A, and an exit stem 1590B. The base stem 1590A can be partially conically shaped. The exit stem 1590B can be cylindrically shaped.

Figure 15B:
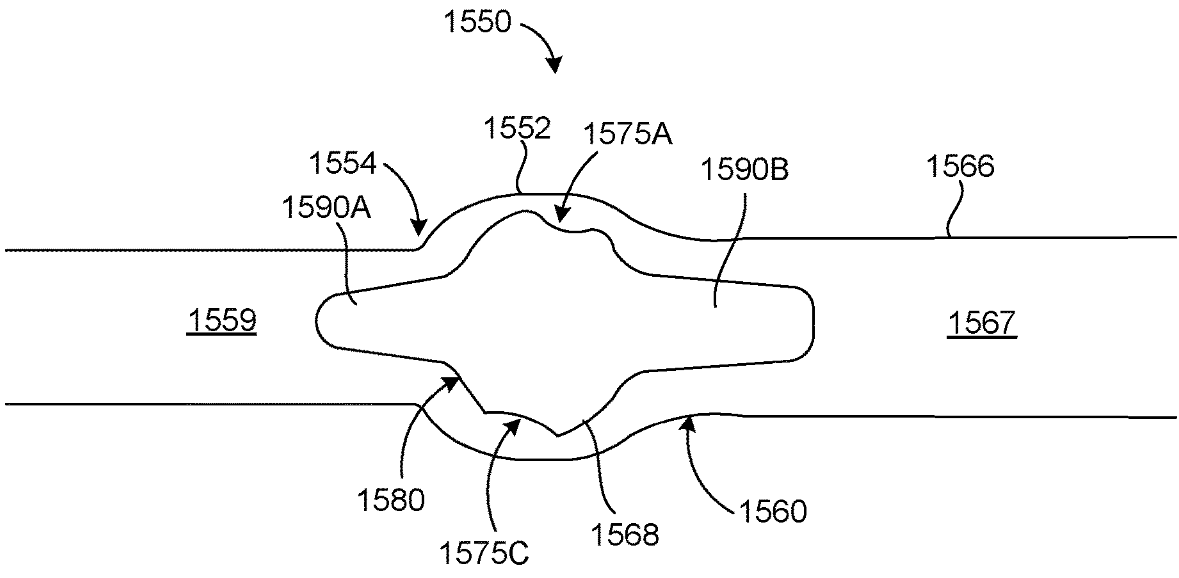
FIG. 15B illustrates a valve that includes the poppet of FIG. 15A according to an aspect.

The cap member 1580 can include a rounded portion facing toward a base 1554 (shown in FIG. 15B). The cap member 1580 can include multiple, such as four, grooves 1575A, 1575B. The grooves 1575A, 1575B can be spaced at equal intervals from each other. The grooves 1575A, 1575B can extend in directions offset between thirty degrees (30°) and sixty degrees (60°) from a direction that the base stem 1590A and/or exit stem 1590B extends from the cap member 1580. The base stem 1590A can extend from the rounded portion of the cap member 1580, through the base 1554, and into an entry passageway 1559 (shown in FIG. 15B). The exit stem 1590B can extend from a portion of the cap member 1580 opposite from the rounded portion, through a tail passageway defined by a tail 1560 (shown in FIG. 15B), and into an exit passageway 1567 (shown in FIG. 14B). The poppet 1568 can define a groove at an intersection of the cap member and the exit stem 1590B. The groove can interface with a biasing member, such as by seating a spring.

FIG. 15B illustrates a valve 1550 that includes the poppet 1568 of FIG. 15A according to an aspect. The valve 1550 can include any combination of features of the valves 150, 1050, 1150, 1250, 1350, 1450 described above. The valve 1550 can be an example of a refill valve 108 or an inflation valve 110.

The valve 1550 can include an entry tube interface 1558. The entry tube interface 1558 can be configured to attach to an entry tube (which can include either of the conduit connectors 103, 105). The entry tube interface 1558 can define an entry passageway 1559 through which fluid flows into the valve 1550. The entry tube interface 1558 can include any combination of features of the entry tube interface 158, 1058, 1158, 1258, 1358, 1458 described above.

The valve 1550 can include a base 1554. The base 1554 can be adjacent to the entry tube interface 1558. The base 1554 can be circular about a longitudinal base axis (not shown in FIG. 15B). The longitudinal base axis can be parallel to a direction from which the entry tube interface 1558 extends from the base 1554. The base 1554 can define a base passageway (not labeled in FIG. 15B). The base 1554 can include any combination of features of the bases 154, 524, 554, 624, 654, 724, 754, 824, 854 924, 954, 1054, 1154, 1254, 1354, 1454 described above.

The valve 1550 can include a bulb 1552. The bulb 1552 can be adjacent to the base 1554. The bulb 1552 can be wider than the base 1554. The bulb 1552 can define a chamber (not labeled in FIG. 15B). The bulb 1552 can include any combination of features of the bulbs 152, 422, 522, 552, 622, 652, 722, 752, 822, 852, 922, 952, 1052, 1152, 1252, 1352, 1452 described above.

The poppet 1568 can be disposed inside the chamber defined by the bulb 1552. The rounded portion of the cap member 1580 of the poppet 1568 can be biased to rest against the base 1554. When the rounded portion of the cap member 1580 of the poppet 1568 is resting against the base 1554, the valve 1550 can be sealed, preventing fluid from flowing through the valve 1550. While not shown in FIG. 15B, the valve 1550 can include a biasing member, such as a spring, biasing the semispherical cap member 1580 of the poppet 1568 to rest against the base 1554. The biasing member can include any combination of features of the biasing members 170, 440, 540, 640, 740, 840, 940 described above.

The valve 1550 can include a tail 1560. The tail 1560 can be adjacent to the bulb 1552. The tail 1560 can be narrower than the bulb 1552. The tail 1560 can define a tail passageway (not labeled in FIG. 15B). The tail 1560 can include and/or define multiple guides (not labeled in FIG. 15B). The multiple guides can extend toward a longitudinal exit axis (not shown in FIG. 15B). The longitudinal exit axis can extend through a center of the tail 1560 parallel to a direction that an exit tube interface 1566 extends from the tail 1560. The multiple guides can be symmetrical about the longitudinal exit axis. The tail 1560 can include any combination of features of the tails 160, 460, 430, 530, 560, 630, 660, 730, 760, 830, 860, 1060, 1160, 1260, 1360, 1460 described above.

The valve 1550 can include the exit tube interface 1566. The exit tube interface 1566 can be adjacent to the tail 1560. The exit tube interface 1566 can be configured to attach to an exit tube (which can include either of the conduit connectors 103, 105). The exit tube interface 1566 can define an exit passageway 1567 through which fluid flows out of the valve 1550. The exit tube interface 1566 can include any combination of features of the exit tube interfaces 166, 466, 1066, 1166, 1266, 1366, 1466 described above.

During high flow conditions into the entry tube interface 1558, pressure against the cap member 1580 can overcome the biasing force on the poppet 1568, and/or cause the portion of the poppet 1568 opposite from the rounded portion that rests against the base 1554 to rest against the guides in the open position. During the high flow conditions, the exit stem 1590B can extend through the tail passageway defined by the tail 1560 and into the exit passageway 1567. The exit stem 1590B can reduce a pressure drop across the cap member 1580, decreasing turbulent flow. The exit stem 1590B can also stabilize and align the poppet 1568 with the guides, isolating vibrations and preventing noise. The grooves 1575A, 1575B can form a helix, forcing the poppet 1568 to rotate, which improves axial alignment of the exit stem 1590B and stabilizes the poppet 1568, reducing noise. The base stem 1590A further reduces a pressure differential across the valve 1550 and maintains axial alignment between the poppet 1568 and the valve 1550.

While certain features of the described implementations have been illustrated as described herein, many modifications, substitutions, changes and equivalents will now occur to those skilled in the art. It is, therefore, to be understood that the appended claims are intended to cover all such modifications and changes as fall within the true spirit of the embodiments of the invention.

What is claimed is:

1. An inflatable penile prosthesis comprising:

a reservoir configured to hold fluid;

an inflatable member; and a pump assembly configured to transfer fluid from the reservoir to the inflatable member, the pump assembly comprising a pump bulb, at least one valve, an entry tube configured to provide the fluid to the at least one valve, and an exit tube configured to send the fluid from the at least one valve, the pump bulb being configured to transfer the fluid from the reservoir, through the at least one valve, and to the inflatable member in response to the pump bulb being compressed, the at least one valve comprising:

an entry tube interface configured to attach to the entry tube and defining an entry passageway;

an entry portion adjacent to the entry tube interface, the entry portion being circular about a longitudinal entry portion axis and defining an entry portion passageway, the longitudinal entry portion axis being parallel to a direction from which the entry tube interface extends from the entry portion;

a middle portion adjacent to the entry portion, the middle portion being wider than the entry portion and defining a chamber;

an exit portion adjacent to the middle portion, the exit portion being narrower than the middle portion, the exit portion defining an exit portion passageway and comprising multiple guides extending toward a longitudinal exit axis, the longitudinal exit axis extending through a center of the exit portion parallel to a direction that an exit tube interface extends from the exit portion, the multiple guides being symmetrical about the longitudinal exit axis;

the exit tube interface adjacent to the exit portion, the exit tube interface being configured to attach to the exit tube, the exit tube interface being narrower than the middle portion, the exit tube interface defining an exit passageway; and a poppet disposed inside the chamber, the poppet being biased to rest against the entry portion.

2. The inflatable penile prosthesis of claim 1, wherein:

the at least one valve includes an inflation valve configured to transfer fluid from the pump assembly to the inflatable member;

the entry tube is attached to the pump bulb and to the entry tube interface of the inflation valve; and the exit tube is attached to the inflatable member and to the exit tube interface of the inflation valve.

3. The inflatable penile prosthesis of claim 1, wherein:

the at least one valve includes a refill valve configured to transfer fluid from the reservoir to the pump bulb;

the entry tube is attached to the reservoir and to the entry tube interface of the refill valve; and the exit tube is attached to the pump bulb and to the exit tube interface of the refill valve.

4. The inflatable penile prosthesis of claim 1, wherein the exit portion comprises three guides at intervals of one hundred twenty degrees (120°) from each other.

5. The inflatable penile prosthesis of claim 1, wherein the exit portion comprises four guides at intervals of ninety degrees (90°) from each other.

6. The inflatable penile prosthesis of claim 1, wherein the at least one valve further includes a biasing member, the biasing member biasing the poppet to rest against the entry portion.

7. The inflatable penile prosthesis of claim 1, wherein the at least one valve further includes a spring, the spring biasing the poppet to rest against the entry portion.

8. The inflatable penile prosthesis of claim 1, wherein the poppet is sphere shaped.

9. The inflatable penile prosthesis of claim 1, wherein the poppet comprises:

a semispherical member; and a partial cone member extending from the semispherical member, the partial cone member extending through the exit portion passageway and into the exit passageway.

10. The inflatable penile prosthesis of claim 1, wherein the poppet comprises:

a cap member, the cap member comprising a rounded portion facing toward the entry portion and a flat portion facing toward the exit portion; and a stem extending from the flat portion of the cap member, the stem extending through the exit portion passageway and into the exit passageway.

11. The inflatable penile prosthesis of claim 10, wherein a widest portion of the stem is adjacent to the cap member.

12. The inflatable penile prosthesis of claim 1, wherein the poppet comprises:

a semispherical member;

a cylindrical member extending from the semispherical member; and a partial cone member extending from the cylindrical member, the partial cone member extending through the exit portion passageway and into the exit passageway.

13. The inflatable penile prosthesis of claim 1, wherein the poppet comprises:

a cap member, the cap member comprising a rounded portion facing toward the entry portion; and a stem extending from a portion of the cap member opposite from the rounded portion, through the exit portion passageway, and into the exit passageway, the cap member defining multiple grooves at equal intervals from each other, the multiple grooves extending in directions offset between thirty degrees (30°) and sixty degrees (60°) from a direction that the stem extends from the cap member.

14. The inflatable penile prosthesis of claim 13, wherein the stem is cylindrically shaped.

15. The inflatable penile prosthesis of claim 13, wherein:

the stem comprises an exit stem; and the poppet further comprises an entry portion stem extending from the rounded portion, through the entry portion, and into the entry passageway.

16. An inflatable penile prosthesis comprising:

a reservoir configured to hold fluid;

an inflatable member; and a pump assembly configured to transfer fluid from the reservoir to the inflatable member, the pump assembly comprising a pump bulb, at least one valve, an entry tube configured to provide the fluid to the at least one valve, and an exit tube configured to send the fluid from the at least one valve, the pump bulb being configured to transfer the fluid from the reservoir, through the at least one valve, and to the inflatable member in response to the pump bulb being compressed, the at least one valve comprising:

an entry tube interface configured to attach to the entry tube and defining an entry passageway;

an entry portion adjacent to the entry tube interface, the entry portion being circular about a longitudinal entry portion axis and defining an entry portion passageway, the longitudinal entry portion axis being parallel to a direction from which the entry tube interface extends from the entry portion;

a middle portion adjacent to the entry portion, the middle portion being wider than the entry portion and defining a chamber;

an exit portion adjacent to the middle portion, the exit portion being narrower than the middle portion, the exit portion defining an exit portion passageway and comprising multiple guides extending toward a longitudinal exit axis, the longitudinal exit axis extending through a center of the exit portion parallel to a direction that an exit tube interface extends from the exit portion, the multiple guides being symmetrical about the longitudinal exit axis;

the exit tube interface adjacent to the exit portion, the exit tube interface being configured to attach to the exit tube, the exit tube interface being narrower than the middle portion, the exit tube interface defining an exit passageway;

a poppet disposed inside the chamber; and a biasing member biasing the poppet to rest against the entry portion.

17. The inflatable penile prosthesis of claim 16, wherein:

the at least one valve includes an inflation valve configured to transfer fluid from the pump assembly to the inflatable member;

the entry tube is attached to the pump bulb and to the entry tube interface of the inflation valve; and the exit tube is attached to the inflatable member and to the exit tube interface of the inflation valve.

18. The inflatable penile prosthesis of claim 16, wherein:

the at least one valve includes a refill valve configured to transfer fluid from the reservoir to the pump bulb;

the entry tube is attached to the reservoir and to the entry tube interface of the refill valve; and the exit tube is attached to the pump bulb and to the exit tube interface of the refill valve.

19. The inflatable penile prosthesis of claim 16, wherein the exit portion comprises four guides at intervals of ninety degrees (90°) from each other.

20. An inflatable penile prosthesis comprising:

a reservoir configured to hold fluid;

an inflatable member; and a pump assembly configured to transfer fluid from the reservoir to the inflatable member, the pump assembly comprising a pump bulb, at least one valve, an entry tube configured to provide the fluid to the at least one valve, and an exit tube configured to send the fluid from the at least one valve, the pump bulb being configured to transfer the fluid from the reservoir, through the at least one valve, and to the inflatable member in response to the pump bulb being compressed, the at least one valve comprising:

an entry tube interface configured to attach to the entry tube and defining an entry passageway;

an entry portion adjacent to the entry tube interface, the entry portion being circular about a longitudinal entry portion axis and defining an entry portion passageway, the longitudinal entry portion axis being parallel to a direction from which the entry tube interface extends from the entry portion;

a middle portion adjacent to the entry portion, the middle portion being wider than the entry portion and defining a chamber;

an exit portion adjacent to the middle portion, the exit portion being narrower than the middle portion, the exit portion defining an exit portion passageway and comprising multiple guides extending toward a longitudinal exit axis, the longitudinal exit axis extending through a center of the exit portion parallel to a direction that an exit tube interface extends from the exit portion, the multiple guides being symmetrical about the longitudinal exit axis;

the exit tube interface adjacent to the exit portion, the exit tube interface being configured to attach to the exit tube, the exit tube interface being narrower than the middle portion, the exit tube interface defining an exit passageway; and a poppet disposed inside the chamber, the poppet being biased to rest against the entry portion, the poppet comprising:

a cap member, the cap member comprising a rounded portion facing toward the entry portion;

an exit stem extending from a portion of the cap member opposite from the rounded portion, through the exit portion passageway, and into the exit passageway, the exit stem being cylindrically shaped; and an entry portion stem extending from the rounded portion, through the entry portion, and into the entry passageway, the cap member defining multiple grooves at equal intervals from each other, the multiple grooves extending in directions offset between thirty degrees (30°) and sixty degrees (60°) from a direction that the exit stem extends from the cap member.

* * * * *